US010682089B2

(12) United States Patent
Kimura et al.

(10) Patent No.: US 10,682,089 B2
(45) Date of Patent: Jun. 16, 2020

(54) INFORMATION PROCESSING APPARATUS, INFORMATION PROCESSING METHOD, AND PROGRAM

(71) Applicant: Sony Corporation, Tokyo (JP)

(72) Inventors: Natsuki Kimura, Tokyo (JP); Yusuke Nakamura, Kanagawa (JP); Akiko Shimizu, Tokyo (JP)

(73) Assignee: Sony Corporation, Tokyo (JP)

(*) Notice: Subject to any disclaimer, the term of this patent is extended or adjusted under 35 U.S.C. 154(b) by 126 days.

(21) Appl. No.: 15/544,549

(22) PCT Filed: Jan. 15, 2016

(86) PCT No.: PCT/JP2016/051072
§ 371 (c)(1),
(2) Date: Jul. 19, 2017

(87) PCT Pub. No.: WO2016/121518
PCT Pub. Date: Aug. 4, 2016

(65) Prior Publication Data
US 2018/0263551 A1 Sep. 20, 2018

(30) Foreign Application Priority Data
Jan. 29, 2015 (JP) ................. 2015-015539

(51) Int. Cl.
*A61B 5/00* (2006.01)
*A61B 5/107* (2006.01)
(Continued)

(52) U.S. Cl.
CPC ............ *A61B 5/442* (2013.01); *A61B 5/0077* (2013.01); *A61B 5/107* (2013.01); *A61B 5/742* (2013.01);
(Continued)

(58) Field of Classification Search
CPC ....... A61B 5/0077; A61B 5/743; A61B 5/444; A61B 5/742; A61B 5/748; A61B 5/7485;
(Continued)

(56) References Cited

U.S. PATENT DOCUMENTS 6,571,003 B1    5/2003   Hillebrand et al.
2003/0063801 A1*  4/2003   Rubinstenn .......... A45D 44/005
                                                382/190
(Continued)

FOREIGN PATENT DOCUMENTS

JP    2001-000419 A    1/2001
JP    2008-293325 A   12/2008
(Continued)

OTHER PUBLICATIONS

International Search Report and Written Opinion and English translation thereof dated Apr. 12, 2016 in connection with International Application No. PCT/JP2016/051072.
(Continued)

*Primary Examiner* — Jingge Wu
(74) *Attorney, Agent, or Firm* — Wolf, Greenfield & Sacks, P.C.

(57) ABSTRACT

The present technology relates to an information processing apparatus, an information processing method, and a program capable of checking a plurality of types of analysis results regarding one skin condition item intuitively and easily.
The information processing apparatus according to one aspect of the present technology includes an acquisition unit configured to obtain information representing a plurality of types of analysis results on skin conditions obtained by analyzing an image of a skin at a same position, and a presentation unit configured to simultaneously display, on a same image, a plurality of types of visualized information obtained from visual representation of the plurality of types
(Continued)

of analysis results. The present technology is applicable to a mobile terminal used together with a skin measurement instrument that photographs a skin image.

11 Claims, 33 Drawing Sheets

(51) Int. Cl.
| | |
|---|---|
| *G16H 10/20* | (2018.01) |
| *G16H 50/70* | (2018.01) |
| *G16H 50/30* | (2018.01) |
| *G16H 30/40* | (2018.01) |
| *G16H 40/63* | (2018.01) |
| *G16H 30/20* | (2018.01) |
| *G06T 7/11* | (2017.01) |
| *G06T 7/00* | (2017.01) |

(52) U.S. Cl.
CPC .............. *G06T 7/0012* (2013.01); *G06T 7/11* (2017.01); *G16H 10/20* (2018.01); *G16H 30/20* (2018.01); *G16H 30/40* (2018.01); *G16H 40/63* (2018.01); *G16H 50/30* (2018.01); *G16H 50/70* (2018.01); *A61B 2576/02* (2013.01); *G06T 2207/30088* (2013.01)

(58) Field of Classification Search
CPC ........... A61B 5/445; A61B 5/442; A61B 5/00; A61B 5/004; A61B 5/0064; A61B 5/107; A61B 5/7435; G06T 2207/30088; G06T 7/0012; G06T 7/11; G06T 7/40
See application file for complete search history.

(56) References Cited

U.S. PATENT DOCUMENTS

| | | | |
|---|---|---|---|
| 2009/0054744 A1 | 2/2009 | Kitamura et al. | |
| 2010/0185064 A1* | 7/2010 | Bandic ................. | A61B 5/0059 600/306 |
| 2011/0116691 A1* | 5/2011 | Chung ................... | A61B 5/442 382/128 |
| 2012/0157821 A1 | 6/2012 | Kitamura et al. | |
| 2014/0243651 A1* | 8/2014 | Kim ...................... | A61B 5/0033 600/407 |
| 2015/0213619 A1* | 7/2015 | Nakamura ........... | A61B 5/0077 382/128 |
| 2016/0125228 A1* | 5/2016 | Son ........................ | A61B 5/442 382/118 |
| 2016/0210764 A1 | 7/2016 | Gomi et al. | |
| 2016/0262624 A1* | 9/2016 | Nakajima .............. | A61B 5/444 |
| 2017/0119301 A1* | 5/2017 | Kimura ................. | G06T 7/0012 |
| 2017/0202504 A1* | 7/2017 | Suzuki .................. | A61B 5/742 |
| 2017/0319065 A1* | 11/2017 | Kimura ................. | A61B 5/684 |

FOREIGN PATENT DOCUMENTS

| | | | |
|---|---|---|---|
| JP | 20082933325 A1 * | 12/2008 | ............ A61B 5/442 |
| JP | 2010-264276 A | 11/2010 | |
| JP | 2012-239768 A | 12/2012 | |
| WO | WO 00/76398 A1 | 12/2000 | |
| WO | WO 2006/118060 A1 | 11/2006 | |
| WO | WO 2014/027522 A1 | 2/2014 | |

OTHER PUBLICATIONS

International Preliminary Report on Patentability and English translation thereof dated Aug. 10, 2017 in connection with International Application No. PCT/JP2016/051072.

* cited by examiner

REPRESENTATION EXAMPLE OF
PORE OPENING:

REPRESENTATION EXAMPLE OF
PORE BLACKHEADS: (BLACKHEAD LEVEL AND SIZE MIXED)

INFORMATION PROCESSING APPARATUS, INFORMATION PROCESSING METHOD, AND PROGRAM

CROSS-REFERENCE TO RELATED APPLICATIONS

This application claims the benefit under 35 U.S.C. § 371 as a U.S. National Stage Entry of International Application No. PCT/JP2016/051072, filed in the Japanese Patent Office as a Receiving Office on Jan. 15, 2016, which claims priority to Japanese Patent Application Number JP 2015-015539, filed in the Japanese Patent Office on Jan. 29, 2015, each of which is hereby incorporated by reference in its entirety.

TECHNICAL FIELD

The present technology relates to an information processing apparatus, an information processing method, and a program, particularly relates to an information processing apparatus, an information processing method, and a program capable of checking a plurality of types of analysis results regarding one skin condition item intuitively and easily.

BACKGROUND ART

There is a technology of analyzing skin conditions by performing image processing on a skin image obtained by photographing the skin. A person who measures the skin condition photographs a measurement portion by applying a measurement instrument including an imaging element, onto the face, or the like, of a person to be measured.

CITATION LIST

Patent Document

Patent Document 1: Japanese Patent Application Laid-Open No. 2012-239768

SUMMARY OF THE INVENTION

Problems to be Solved by the Invention

As the skin conditions, conditions of each of items of texture, pores, spots, and color tones, or the like, are analyzed on the basis of a skin image. A person who performs measurement or a person to be measured can select a desired item for checking and can check an analysis result regarding the selected item.

Normally, the analysis result on one item is represented by a plurality of pieces of information, such that pore conditions are represented by, for example, a pore opening condition and a pore blackhead condition.

Provided that user interface (UI) images representing information on individual analysis results are displayed separately, it would be difficult to check the relationship between each of the analysis results, or the like.

The present technology is made in view of this situation and intended to achieve checking a plurality of types of analysis results regarding one skin condition item intuitively and easily.

Solutions to Problems

The information processing apparatus according to one aspect of the present technology includes an acquisition unit configured to obtain information representing a plurality of types of analysis results on skin conditions obtained by analyzing an image of a skin at a same position, and a presentation unit configured to simultaneously display, on a same image, a plurality of types of visualized information obtained from visualized representation of the plurality of types of analysis results.

On the presentation unit, it is possible to display the visualized information on the image of the skin used for obtaining the analysis result.

On the presentation unit, it is possible to display the visualized information representing the plurality of types of analysis results obtained by analyzing the image of the skin at a selected position in accordance with the selection of the position of the skin.

On the presentation unit, it is possible to simultaneously display the plurality of images that displays the plurality of types of visualized information.

On the presentation unit, it is possible to display the visualized information representing the plurality of types of analysis results associated with a selected item during selection of one item among the plurality of items related to skin conditions.

On the presentation unit, in a case where a pore item is selected, it is possible to display the visualized information representing the analysis result on pore opening and the visualized information representing the analysis result on pore blackhead.

On the presentation unit, in a case where a spot item is selected, it is possible to display individually the visualized information representing the analysis result on different types of spots.

It is possible to further provide an analysis unit configured to analyze skin conditions on the basis of the skin image.

It is possible to cause the analysis unit to calculate the amount of predetermined component of the skin at individual positions on the skin image, specify a position on which the amount of predetermined component is locally large on the basis of the amount of predetermined component, and output information representing the amount of predetermined component in a region including the specified position, as the analysis result.

According to one aspect of the present technology, information representing a plurality of types of analysis results on skin conditions obtained by analyzing an image of the skin at a same position is obtained, and a plurality of types of visualized information obtained from visualized representation of the plurality of types of analysis results is simultaneously displayed on a same image.

Effects of the Invention

According to the present technology, it is possible to check a plurality of types of analysis results regarding one skin condition item intuitively and easily.

Note that effects described herein are non-limiting. The effects may be any effects described in the present disclosure.

MODE FOR CARRYING OUT THE INVENTION

Figure 1:
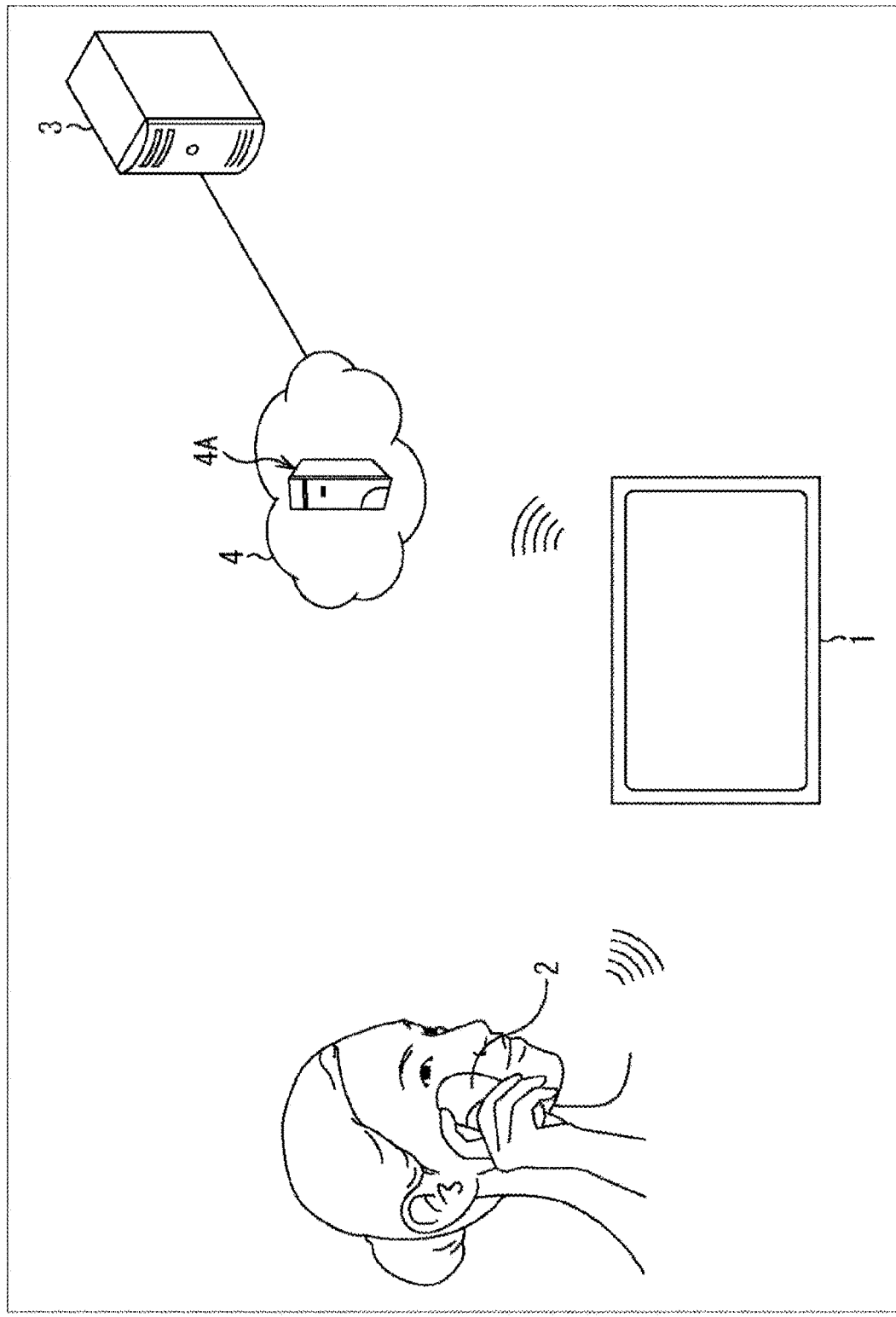
FIG. 1 is a diagram illustrating an exemplary configuration of a skin analysis system according to the present technology.

Hereinafter, embodiments of the present technology will be described. Description will be presented in the following order.

First embodiment (exemplary skin condition analysis performed by server)
1. Configuration of skin analysis system
2. First example of measurement result display screen
3. Second example of measurement result display screen
4. Third example of measurement result display screen
5. Configuration of individual devices
6. Operation of individual devices
Second embodiment (exemplary skin condition analysis performed by information processing terminal)
Modification example First Embodiment <1. Configuration of Skin Analysis System>

FIG. 1 is a diagram illustrating an exemplary configuration of a skin analysis system according to the present technology.

The skin analysis system in FIG. 1 includes an information processing terminal 1, a skin measurement instrument 2, and an analysis server 3. The information processing terminal 1 and the analysis server 3 are connected with each other via a network 4 such as the Internet. The information processing terminal 1 is connected with the network 4 via a relay apparatus 4A such as a Wi-Fi (registered trademark) router.

The information processing terminal 1 and the skin measurement instrument 2 are connected with each other via wireless communication such as a wireless local area network (LAN). The information processing terminal 1 and the skin measurement instrument 2 may be connected with each other via wired communication using a universal serial bus (USB) cable, or the like. It is also allowable such that the skin measurement instrument 2 is directly connected to the network 4 and that the skin measurement instrument 2 and the analysis server 3 can communicate with each other.

The skin analysis system in FIG. 1 is used by a user (mainly on one's own) to measure own skin conditions and check measurement results. The user can be a person who measures skin conditions and can be a person whose skin conditions are measured. Measurement of skin conditions is sometimes performed by a third party such as a cosmetic staff member.

The information processing terminal 1 is a tablet terminal. A display such as a liquid crystal display (LCD) is provided on a housing of the information processing terminal 1. The display includes a touch panel. The user can directly touch and operate on a button, or the like, displayed on the display. It is also allowable to include other mobile terminals such as a personal computer, a smartphone, a mobile phone, personal digital assistants (PDA), a head mounted display (HMD) to be used as the information processing terminal 1.

The information processing terminal 1 obtains a skin image photographed by the skin measurement instrument 2. The skin image is an enlarged image of a skin of a predetermined position such as the user's face. The skin image of a measurement point such as the forehead, the cheek, and a mouth region, is obtained by the information processing terminal 1.

It is also possible to set an entire face as the measurement point instead of the small range such as the forehead, the cheek, and the mouth region. In this case, the image including the entire face of the user, photographed by a camera that can photograph the entire face, is obtained as the skin image by the information processing terminal 1.

The skin measurement instrument 2 is an electronic device of a size that can be held by the user with one hand. The skin measurement instrument 2 includes various sensors such as an imaging element and a temperature sensor. Now, the configuration of the skin measurement instrument 2 will be described briefly.

Figure 2:
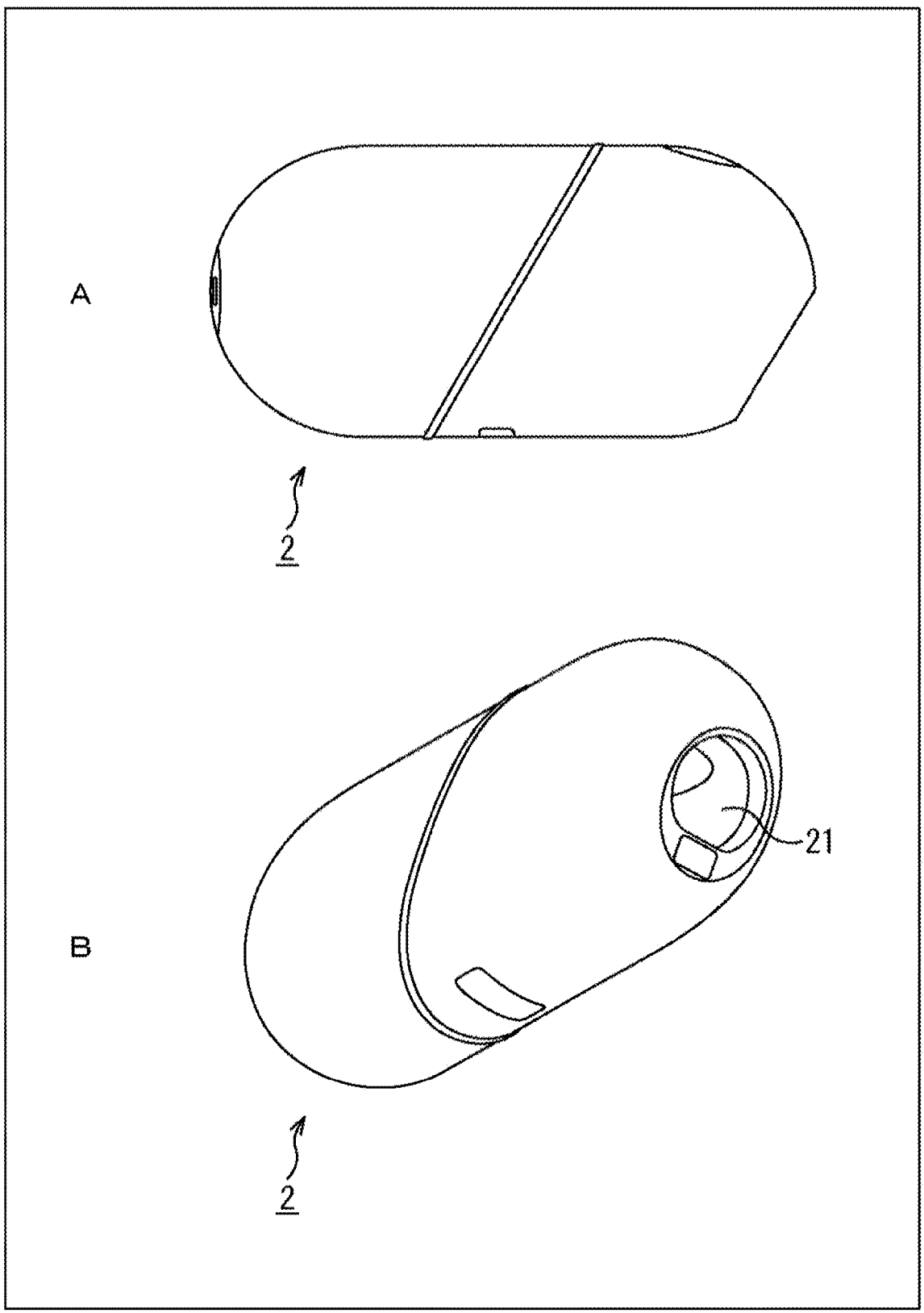
FIG. 2 is an external view of a skin measurement instrument.

FIG. 2 is an external view of the skin measurement instrument 2.

As illustrated in A of FIG. 2, the skin measurement instrument 2 includes a housing having a substantially horizontally long elliptic shape in side view. A flat surface is formed at a position slightly shifted from a top portion at a right edge of the housing, and a hole portion 21 having a substantially circular shape is formed on this flat surface, as illustrated in B of FIG. 2. The skin measurement instrument 2 is generally configured with a curved surface, other than the portion around the hole portion 21 of the housing.

The inner portion of the hole portion 21 includes an illumination unit that emits light toward the outside of the hole portion 21, an imaging element that performs photographing after receiving reflected light, or the like. When the user measures one's own skin conditions by photographing while applying the hole portion 21 onto a portion to be measured.

Figure 3:
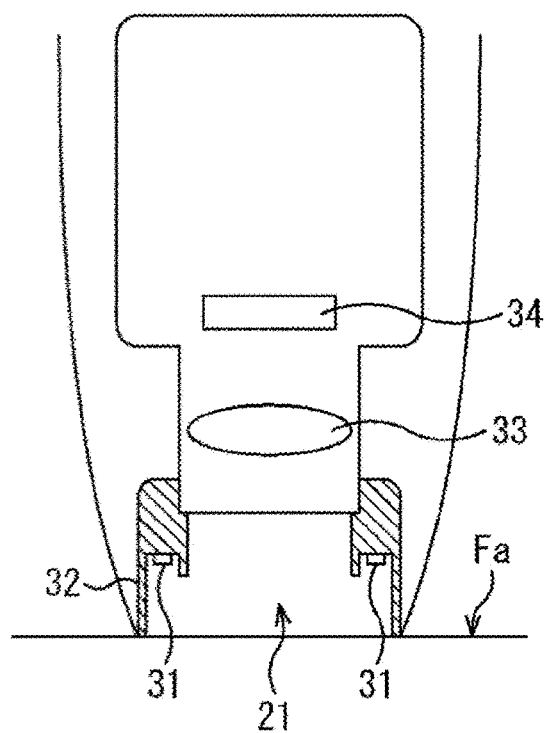
FIG. 3 is a cross-sectional view illustrating an exemplary configuration of an interior of the skin measurement instrument.

FIG. 3 is a cross-sectional view illustrating an exemplary configuration of an interior of the skin measurement instrument 2.

The skin measurement instrument 2 includes an illumination unit 31, a cylinder portion 32, a lens 33, and an imaging element 34. The lens 33 and the imaging element 34 are provided inside the housing. The illumination unit 31 is provided inside the cylinder portion 32.

The light emitted from the illumination unit 31 reaches a skin surface Fa. Moreover, the light reflected by the skin surface Fa passes through the lens 33 and reaches the imaging element 34. When the cylinder portion 32 is in close contact with the skin surface Fa at this time, it is possible to prevent the light emitted from the illumination unit 31 from leaking to the outside of the skin measurement instrument 2. Moreover, it is possible to prevent the light entering the inside of the skin measurement instrument 2 from reaching the imaging element 34.

Figure 4:
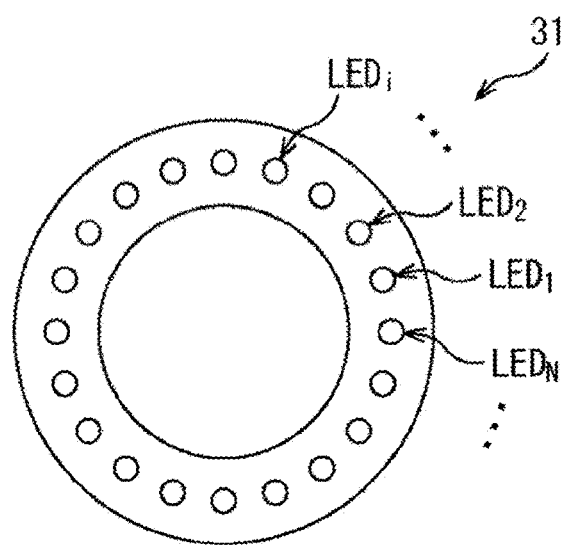
FIG. 4 is a diagram illustrating an exemplary configuration of an illumination unit.

FIG. 4 is a diagram illustrating an exemplary configuration of the illumination unit 31.

The illumination unit 31 is configured with light emitting diodes $(LED)_1$ to $LED_N$ as a plurality of light sources, arranged in a ring shape. The type of light source is not limited to the LED. By providing each of the LEDs with a polarizing filter, or the like, as appropriate, it would be possible to achieve photographing under different photographing conditions such as a different wavelength.

The information processing terminal 1 in FIG. 1 transmits a skin image obtained from the above-configured skin measurement instrument 2 to the analysis server 3 and causes the analysis server 3 to analyze the skin conditions. A plurality of skin images photographed under different conditions is transmitted to the analysis server 3.

The analysis server 3 analyzes user's skin conditions on the basis of the skin image transmitted from the information processing terminal 1. The analysis server 3 transmits information representing skin condition analysis results to the information processing terminal 1. For example, analysis is performed on a plurality of items regarding the skin conditions, such as texture, pore, spots, and the color tone. The analysis server 3 functions as an information processing apparatus that analyzes skin conditions by performing image processing on the skin image.

The information processing terminal 1 receives information transmitted from the analysis server 3 and displays a measurement result display screen, on the display. The measurement result display screen is a screen that displays skin condition analysis results. As described later, it would be also allowable to cause the information processing terminal 1 itself to perform skin condition analysis and to display the measurement result display screen.

<2. First Example of Measurement Result Display Screen>

Figure 5:
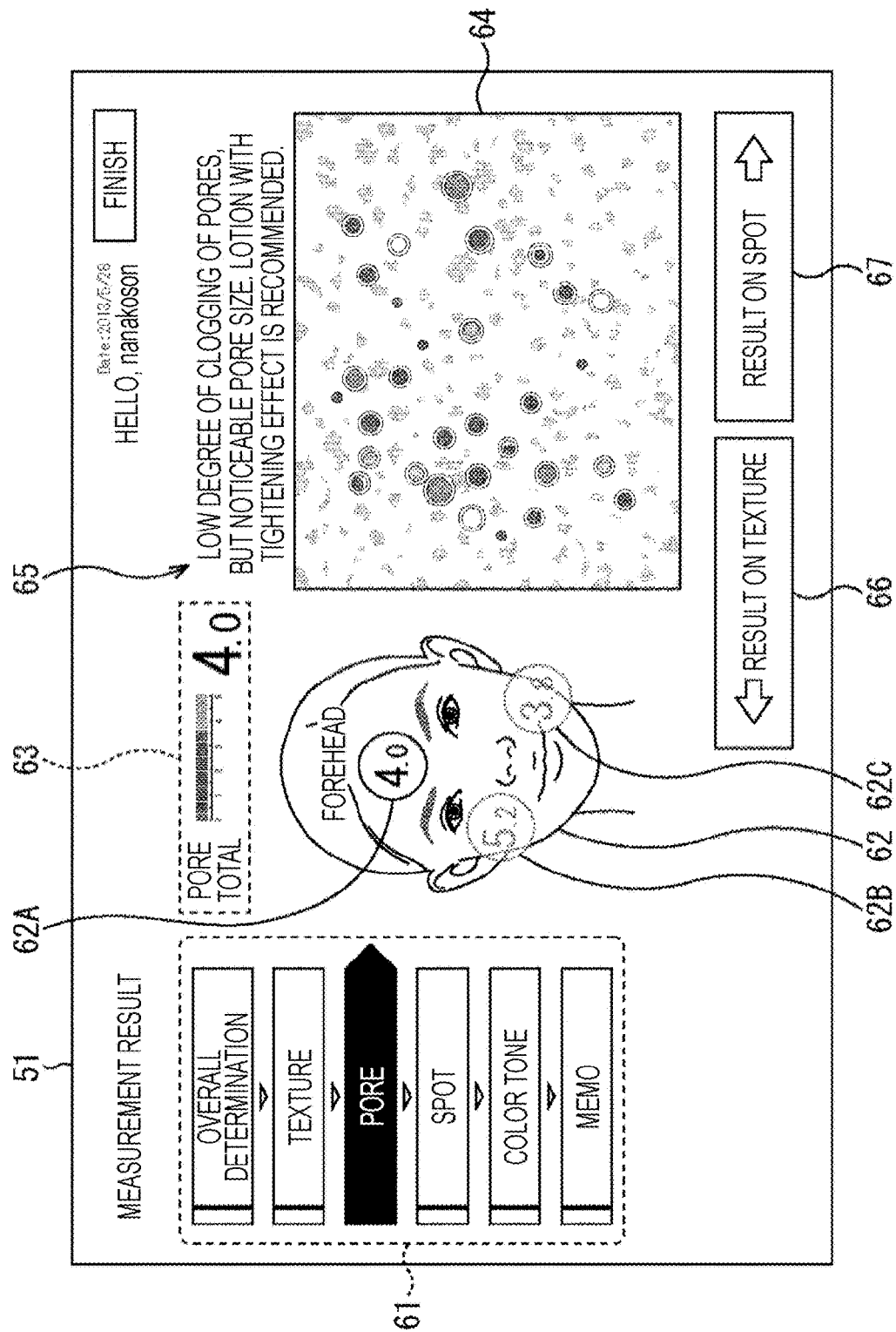
FIG. 5 is a diagram illustrating an exemplary measurement result display screen.

FIG. 5 is a diagram illustrating an exemplary measurement result display screen. The layout of elements constituting the measurement result display screen can be changed as appropriate.

The measurement result display screen in FIG. 5 is a screen displayed on a display 51 of the information processing terminal 1. A tab 61 is displayed on the left of the measurement result display screen. The tab 61 is a tab for each of the items related to skin conditions. The tab 61 is configured with tabs with texts indicating "overall determination", "texture", "pore", "spot", "color tone", and "memo". Note that the broken line enclosing the tab 61, etc., is drawn for convenience of explanation and is not actually displayed.

In an example in FIG. 5, the tab for the item "pore" is selected. The measurement result display screen in FIG. 5 is a screen that displays an analysis result regarding the item "pore".

An illustration 62 of the face of a person facing front is displayed at a position in a center, a little closer to the left on the measurement result display screen. An icon 62A is displayed at a position of the forehead in the illustration 62, while an icon 62B is displayed at a position of the cheek. Moreover, an icon 62C is displayed at a position in the mouth region. A score indicating the pore condition at each of the positions is displayed on each of the icons 62A to 62C.

In the example in FIG. 5, the icon 62A is selected and displayed with the color different from the colors of the icons 62B and 62C. An analysis result of pore conditions of the forehead obtained on the basis of the skin image of the forehead is displayed on the measurement result display screen in FIG. 5.

When the skin image is photographed, a screen of guiding photographing of skin images in the order of the forehead, the cheek, and the mouth region, is displayed on the display 51, for example. By performing photographing following the screen, the information processing terminal 1 and the analysis server 3 can specify which skin image has been obtained by photographing which position of the skin.

A score 63 indicating overall estimation regarding pore conditions is displayed on an upper portion of the illustration 62. The score 63 is configured with an indicator and a number representing the score. It is allowable to configure to display solely the number representing the score, without displaying the indicator.

An analysis result display image 64 is displayed on the right of illustration 62. The analysis result display image 64 is an image that simultaneously displays a plurality of types of information representing forehead pore analysis results. This means a plurality of types of analysis results representing pore conditions is displayed by one image. As described later in detail, the analysis result display image 64 displays an analysis result on pore opening and an analysis result on pore blackhead.

Note that it is also possible to display solely the desired type of information on the analysis result display image 64 instead of simultaneously displaying the plurality of types of information representing the analysis results. For example, check buttons are provided to be used for selecting whether to display the analysis result for each of the types of analysis result, being displayed below the analysis result display image 64. The user can switch the types of analysis result to be displayed on the analysis result display image 64 by operating the check buttons.

A comment 65 is displayed above the analysis result display image 64. The comment 65 is text information regarding pore conditions of the forehead, a care method, or the like.

The user can switch the displays of analysis results by operating the icons 62A to 62C. In a case where the icon 62B is operated in the state of FIG. 5 in which the item "pore" is selected, an image representing an analysis result on cheek pore opening and an analysis result on cheek blackhead is displayed as the analysis result display image 64. Moreover, in a case where the icon 62C is operated, an image representing an analysis result on pore opening in the mouth region and an analysis result on the pore blackhead in the mouth region is displayed as the analysis result display image 64. The content of the comment 65 is switched together with the switching of the display of the analysis result display image 64.

A previous button 66 and a next button 67 are displayed below the analysis result display image 64. The previous button 66 is a button operated to return to a previous item. The next button 67 is a button operated to proceed to a next item.

Now, the analysis result display image 64 will be described with reference to FIGS. 6 and 7.

Figure 6:
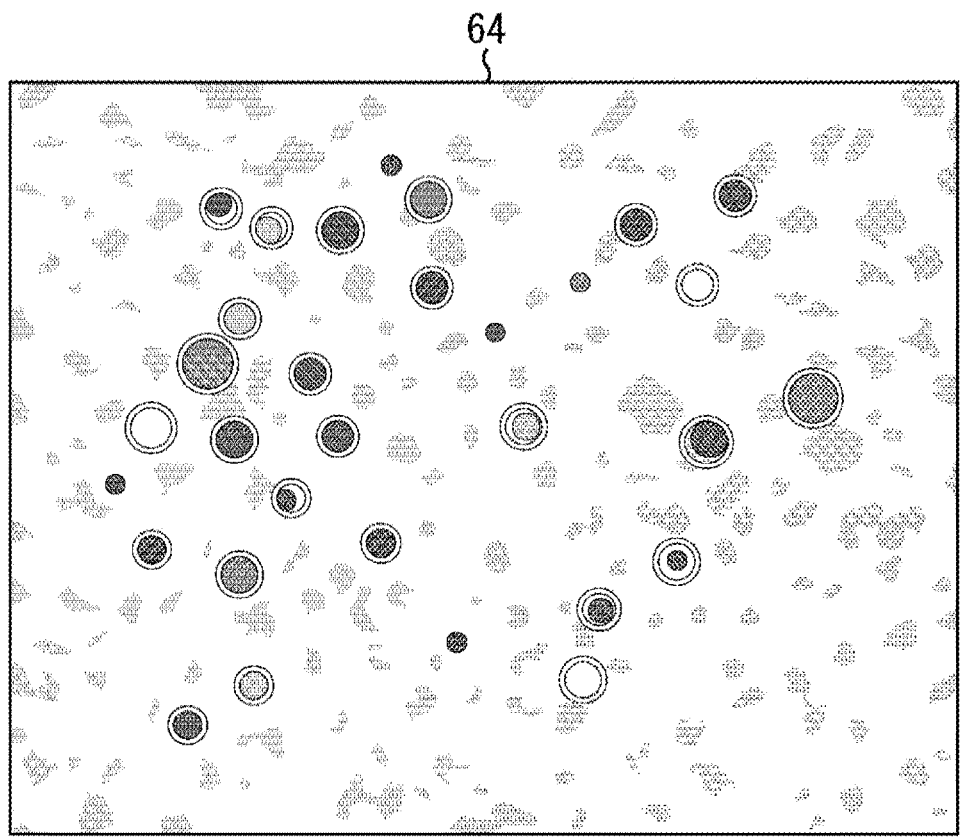
FIG. 6 is an enlarged view of an analysis result display image.

FIG. 6 is an enlarged view of the analysis result display image 64. FIG. 7 is a diagram separately illustrating information constituting the analysis result display image 64 in FIG. 6.

Figure 7:
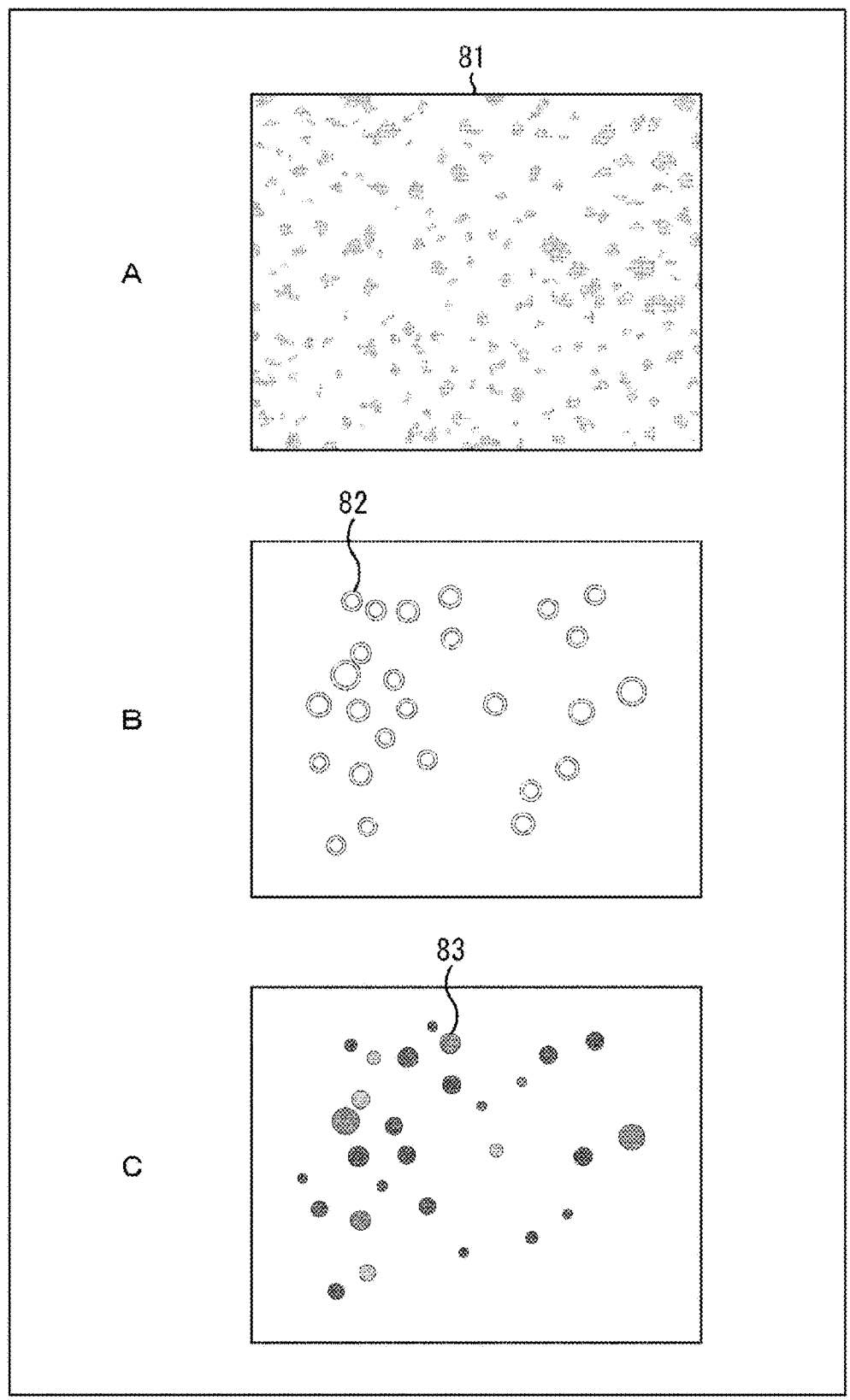
FIG. 7 is a diagram illustrating information constituting the analysis result display image in FIG. 6.

An image 81 in A of FIG. 7 is a skin image. In a case, as illustrated in FIG. 5, where the forehead is selected as the position for the pore condition display, the image 81 illustrates the skin image of the forehead.

An image 82 in B of FIG. 7 is an image as visualized information representing a visualized pore opening analysis result. As illustrated in B of FIG. 7, the pore is represented by an image of an open circle. Moreover, the pore opening degree is represented by the size of the open circle.

Figure 8:
FIG. 8 is a diagram illustrating an exemplary representation of a pore opening degree.

FIG. 8 is a diagram illustrating an exemplary representation of a pore opening degree.

As illustrated in FIG. 8, the pore opening degree is represented by six stages, for example. Higher the opening degree, the larger circular image is allocated as the image 82. The image 82 may either be displayed in a single color or different colors in accordance with the stage of opening. The shape of the image representing the pore opening degree is not limited to the circle but may be other shapes such as a square and a triangle.

By analyzing the skin image, the position and the opening degree of the pore are specified, and the image 82 of the size that corresponds to the specified opening degree is displayed at a specified pore position regarding the pore that opens to a degree of a threshold or above, for example.

An image 83 in C of FIG. 7 is an image as visualized information representing a visualized pore blackhead analysis result. As illustrated in C of FIG. 7, pores are represented by a circular image filled with a predetermined color. Moreover, the pore blackhead degree is represented by the change in color. The blackhead degree is represented by changing the density of a predetermined color, or changing the transmittance, for example. The blackhead degree may be represented by changing both the density and the transmittance.

Figure 9:
FIG. 9 is a diagram illustrating an exemplary representation of a pore blackhead degree.

FIG. 9 is a diagram illustrating an exemplary representation of the pore blackhead degree.

As illustrated in FIG. 9, the pore blackhead degree is represented by six stages, for example. The higher the blackhead degree, an image of the darker color or an image with the lower transmittance is allocated as the image 83. Note that the size of the circle represents the size of the pore in C of FIG. 7 and in FIG. 9.

By analyzing the skin image, the pore position, the pore size, and the pore blackhead degree are specified. Regarding the pore that includes a blackhead to a degree of a threshold or above, the image 83 of the color that corresponds to the specified blackhead degree is displayed with the specified size at a specified position of the pore.

The analysis result display image 64 is configured with the image 82 in B of FIG. 7, representing a visualized pore opening analysis result and the image 83 in C of FIG. 7, representing a visualized pore blackhead analysis result displayed on the image 81 in A of FIG. 7 as the skin image.

In this manner, the pore opening condition and the pore blackhead condition are analyzed individually as pore analysis results, and are simultaneously displayed on the same image.

The information processing terminal 1 can represent four pore conditions of wide opening with a blackhead, wide opening without any blackhead, no wide opening with a blackhead, and no wide opening without any blackhead. The user can intuitively check the pore opening condition and the pore blackhead condition individually.

Moreover, since the information representing the plurality of types of analysis results regarding the pore is simultaneously displayed on one image, the user can check the pore condition more intuitively and easily compared with a case where individual pieces of information are displayed separately. Moreover, the user can check the relationship between the pore opening and the pore blackhead by comparing individual pieces of information with each other.

Since the types of analysis result can be switched by operation of the check buttons, the user can select solely a desired item for comparison, at situations such as before/after comparison.

<3. Second Example of Measurement Result Display Screen>

Figure 10:
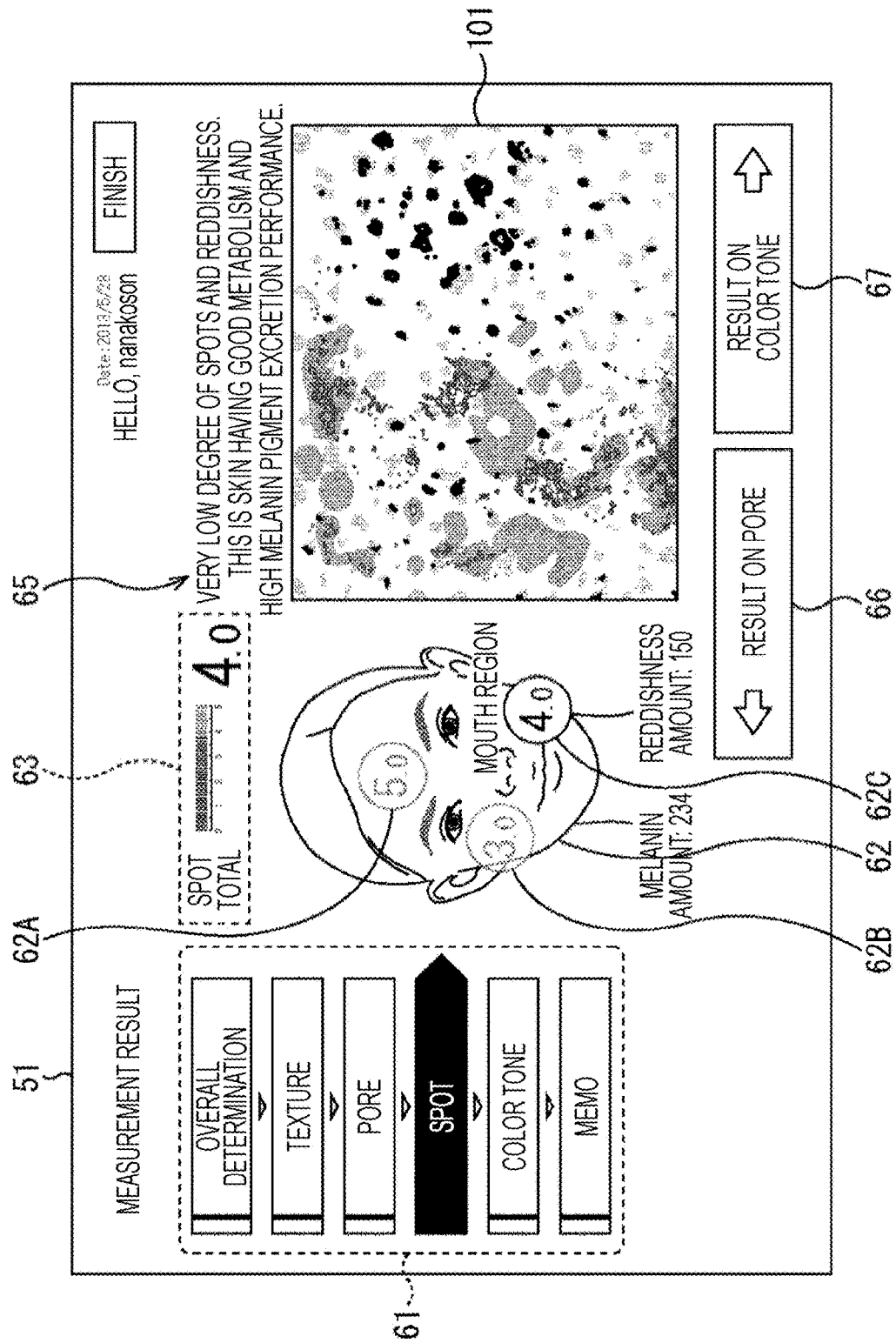
FIG. 10 is a diagram illustrating another exemplary measurement result display screen.

FIG. 10 is a diagram illustrating another exemplary measurement result display screen.

The measurement result display screen in FIG. 10 is a screen that displays an analysis result regarding the item "spot". In an example in FIG. 10, the tab for the item "spot" is selected, among the tab 61. The score 63 displays overall estimation regarding the spot.

Each of the icons 62A to 62C displayed on the illustration 62 represents the score of spot conditions at each of the positions of the forehead, the cheek, and the mouth region. In the example in FIG. 10, the icon 62C is selected and displayed with the color different from the colors of the icons 62A and 62B. An analysis result on spot conditions in the mouth region obtained on the basis of the skin image of the mouth region is displayed on the measurement result display screen in FIG. 10. Selection/non-selection of the icons may be represented by other expressions such as a difference in texture and thickness of the frame, other than the color.

An analysis result display image 101 is displayed on the right of the illustration 62. The analysis result display image 101 is an image that simultaneously displays a plurality of types of information representing mouth region spot analysis results. This means a plurality of types of analysis results representing spot conditions is displayed by one image. The analysis result display image 101 represents an analysis result of a reddish spot and an analysis result of a melanin spot. Spot types include a reddish spot and a melanin spot, for example.

The reddish spot is a spot partially including a reddish portion. This spot is sometimes caused by inflammation such as acne. The reddish spot portion is specified as a portion having a large amount of hemoglobin in the blood.

In contrast, the melanin spot is a spot that is partially brownish. This is sometimes caused by excessive generation of melanin by exposure to the UV, or the like. The melanin spot portion is specified as a portion having a large amount of melanin.

In a case where the icon 62A is operated in a state of FIG. 10 in which the item "spot" is selected, an image representing an analysis result on a reddish spot on the forehead and an analysis result on a melanin spot on the forehead is displayed as the analysis result display image 101. Moreover, in a case where the icon 62B is operated, an image representing an analysis result on a reddish spot on the cheek and an analysis result on a melanin spot on the cheek is displayed as the analysis result display image 101. The content of the comment 65 regarding the condition of "spot", a care method, or the like is switched together with the switching of the display of the analysis result display image 101.

Now, the analysis result display image 101 will be described with reference to FIGS. 11 and 12.

Figure 11:
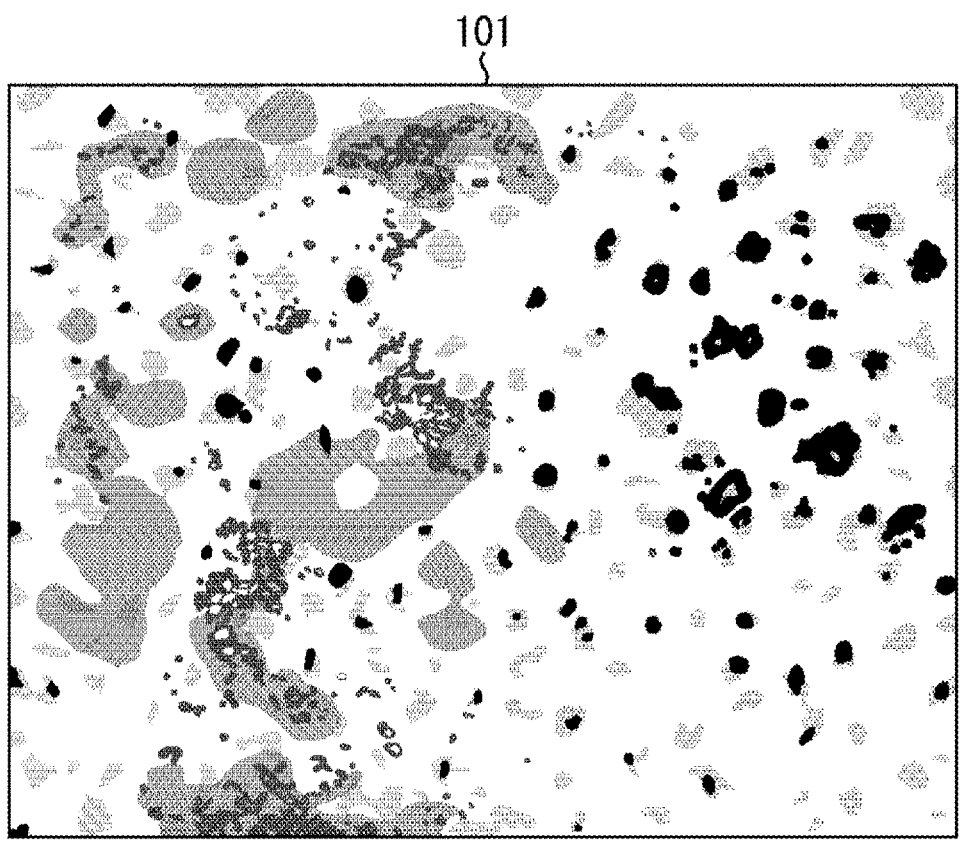
FIG. 11 is an enlarged view of the analysis result display image.

FIG. 11 is an enlarged view of the analysis result display image 101. FIG. 12 is a diagram separately illustrating information constituting the analysis result display image 101 in FIG. 11.

Figure 12:
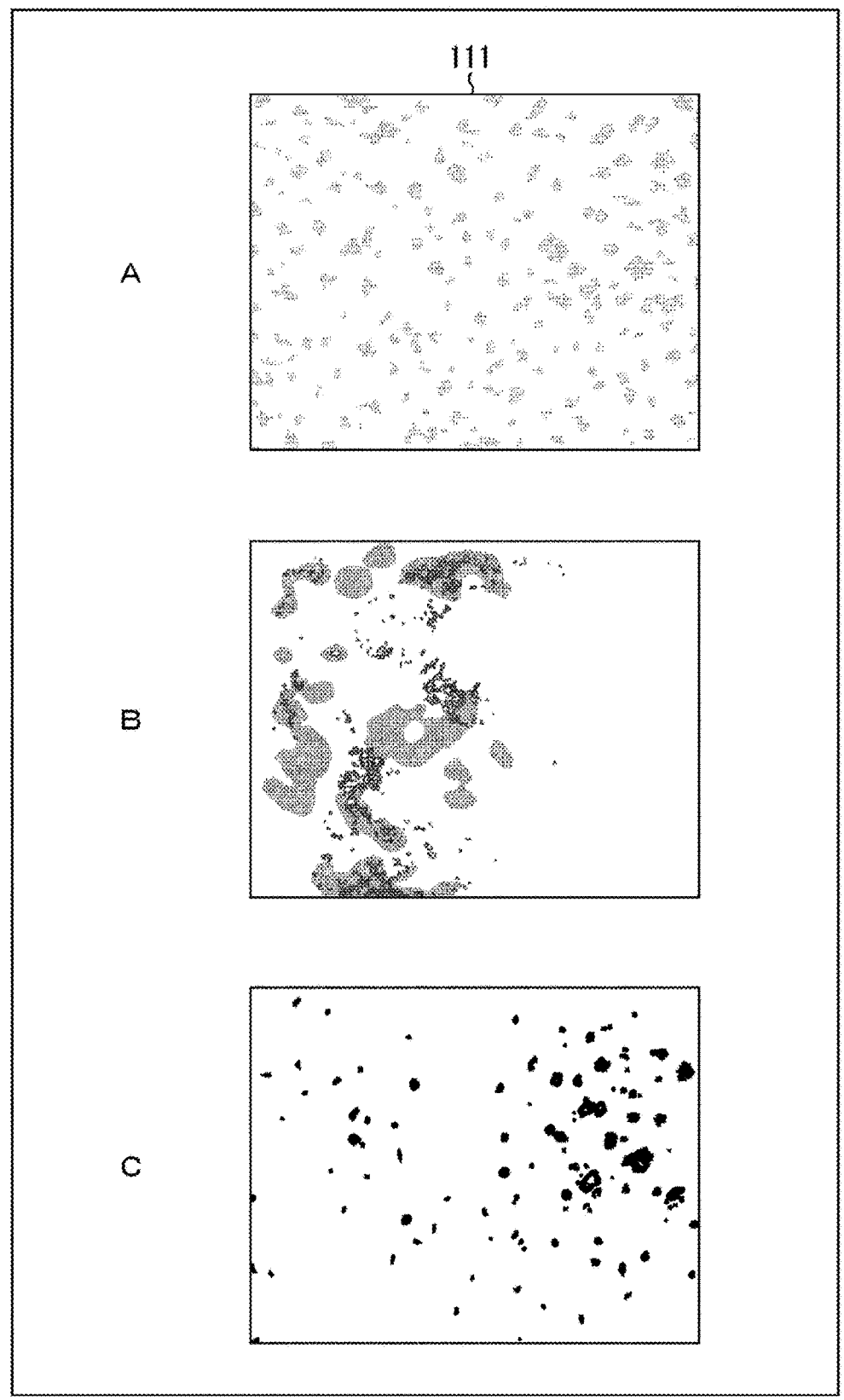
FIG. 12 is a diagram illustrating information constituting the analysis result display image in FIG. 11.

An image 111 in A of FIG. 12 is a skin image. In a case, as illustrated in FIG. 10, where the mouth region is selected as the position for the spot condition display, the image 111 illustrates the skin image of the mouth region.

An image in B of FIG. 12 is an image as visualized information representing a visualized reddish spot analysis result. As illustrated in B of FIG. 12, distribution of hemoglobin that causes the reddish spot is represented by distribution of dots of a predetermined color such as red. Hemoglobin distribution can be represented by coloring the region instead of distribution of dots.

In a case where distribution of hemoglobin at each of depths can be measured by changing the intensity and wavelength of the light emitted at photographing of the skin image, the distribution of hemoglobin at each of the depths may be represented by different dot contrasts. In the image in B of FIG. 12, the difference in contrast (difference in shades) of the red dot represents the difference in depth where hemoglobin exists. The portion of dots with a high contrast is the portion where a large amount of hemoglobin exists at a shallow position from the epidermis, while the portion of dots with a low contrast is the portion where a large amount of hemoglobin exists at a deep position from the epidermis.

An image in C of FIG. 12 is an image as visualized information representing a visualized melanin spot analysis result. As illustrated in C of FIG. 12, distribution of melanin that causes the melanin spot is represented by distribution of dots of a color different from the color representing the distribution of the reddish spot, such as blue. Melanin distribution can be represented by coloring the region instead of distribution of dots.

In a case where distribution of melanin at each of depth can be measured, the distribution of melanin at each of the depths may be represented by different dot contrasts. In the image in C of FIG. 12, the difference in contrast of the blue dot represents the difference in depth where melanin exists.

The analysis result display image 101 is configured with the image in B of FIG. 12, representing visualized reddish spot analysis result and the image in C of FIG. 12, representing visualized melanin spot analysis result displayed on the image 111 in A of FIG. 12 as the skin image.

In this manner, reddish spot condition and melanin spot condition are analyzed individually as spot analysis results, and are simultaneously displayed on the same image.

Moreover, since a plurality of types of information representing the spot conditions such as the reddish spot condition and the melanin spot condition is simultaneously displayed on one image, the user can check the spot condition more intuitively and easily compared with a case where individual pieces of information are displayed separately. Moreover, the user can check the relationship between the reddish spot and the melanin spot by comparing individual pieces of information with each other.

Since the types of analysis result can be switched by operation of the check buttons, the user can select solely a desired item for comparison, at situations such as before/after comparison.

<4. Third Example of Measurement Result Display Screen>

While the above-described configuration is a case where the plurality of types of analysis results associated with one item such as "pore" or "spot" is displayed on one image, it would be also possible to collectively display the analysis result associated with a plurality of items, on one image.

Figure 13:
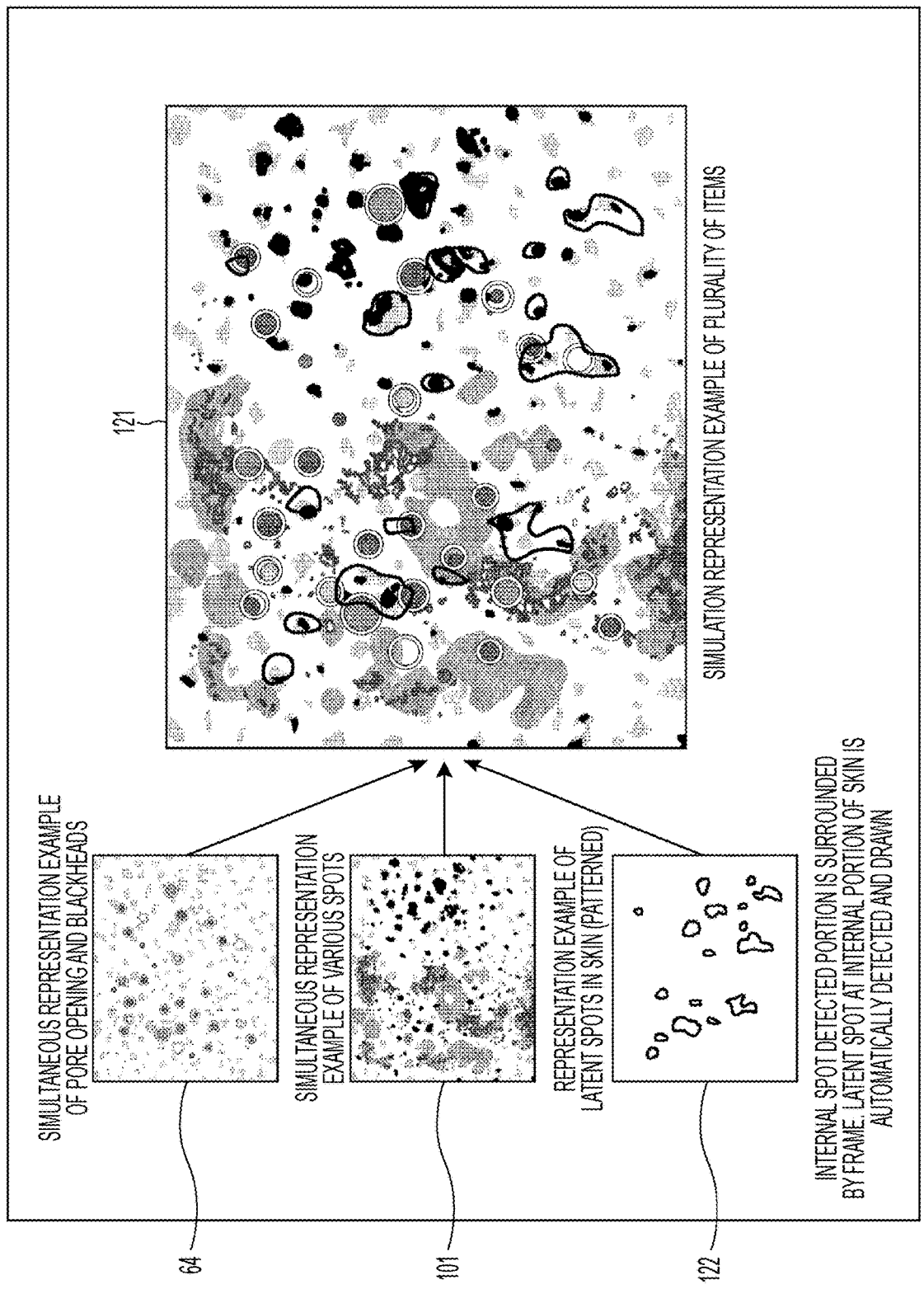
FIG. 13 is an exemplary analysis result display image.

FIG. 13 is an exemplary analysis result display image.

An analysis result display image 121 is an image combining the analysis result display image 64 representing an analysis result of "pore", the analysis result display image 101 representing an analysis result of "spot", and an image 122, with each other. All of the analysis result display image 64, the analysis result display image 101, and the image 122 are images representing analysis results on the skin image at a same position.

The image 122 is an image representing an analysis result of an internal spot. A range enclosed by a line with a predetermined color corresponds to the range where the emergence of a spot in the future is predicted. The range of the internal spot is specified, in the analysis of a skin image, by obtaining, for example, the difference between the range of a spot at a shallow portion such as a melanin spot, and the range of a spot at a deep portion, and by determining solely the range of the spot at the deep portion as the range of the internal spot.

In this manner, the user can collectively check the analysis results on the plurality of items by collectively displaying the analysis results associated with the plurality of items, on one image. Moreover, this also enables the user to check the causal relationship between each of the items, such as the relationship between the pore condition and the spot condition.

Figure 14:
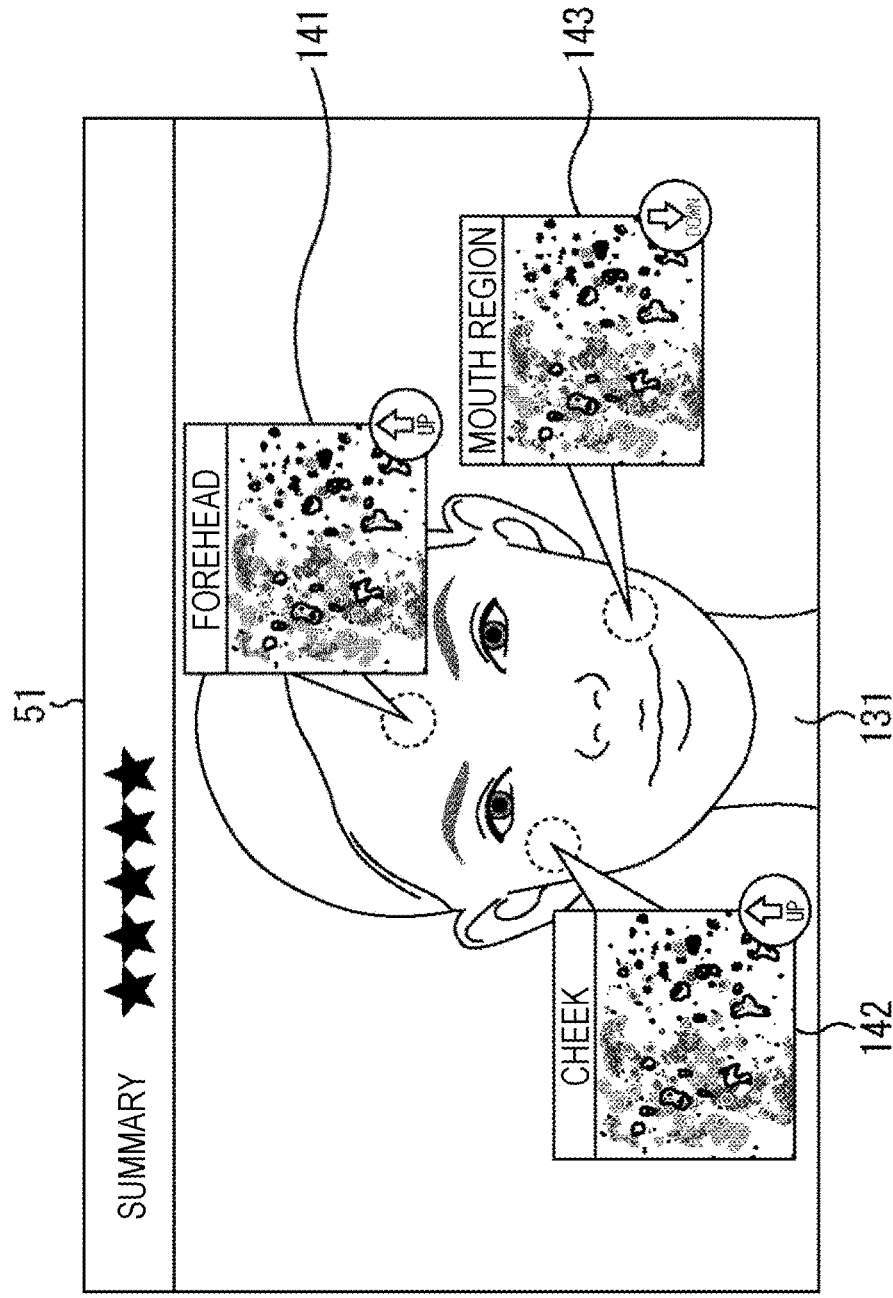
FIG. 14 is a diagram illustrating an exemplary measurement result display screen.

FIG. 14 is a diagram illustrating an exemplary measurement result display screen using an analysis result display image that collectively displays analysis results on a plurality of items.

The measurement result display screen in FIG. 14 is displayed when the "overall determination" tab is selected, for example.

An illustration 131 of the face of a person facing front is displayed at substantially a central position of the measurement result display screen. Analysis result display images 141 to 143 are superimposed and displayed over the illustration 131 with each of the positions of the person's forehead, cheek, and mouth region as sources of the balloon portions.

The analysis result display image 141 is an image representing an analysis result on "pore", an analysis result on "spot", and an analysis result on a range of an internal spot, obtained by analyzing a skin image of the forehead.

Similarly, the analysis result display image 142 is an image representing an analysis result on "pore", an analysis result on "spot", and an analysis result on a range of an internal spot, obtained by analyzing a skin image of the cheek.

The analysis result display image 143 is an image representing an analysis result on "pore", an analysis result on "spot", and an analysis result on a range of an internal spot, obtained by analyzing a skin image of the mouth region.

In this manner, by displaying an image representing analysis results on the plurality of items for the plurality of positions, on the same screen, the user can comprehensively check the skin conditions at each of the positions on the face.

Note that, in a case where the item of "texture" is selected on the measurement result display screen in FIG. 5, for example, information representing a visualized analysis result on the width of sulcus cutis, information representing a visualized analysis result on the width of crista cutis, information representing a visualized analysis result on the area of crista cutis, and information representing a visualized analysis result on the shape of crista cutis are displayed on one image. The item of "texture" is associated with the analysis result on the width of sulcus cutis, the analysis result on the width of crista cutis, the analysis result on the area of crista cutis, and the analysis result on the shape of crista cutis.

Processing of implementing the above-described displays on the information processing terminal 1 and the analysis server 3 will be described later with reference to a flowchart.

<5. Configuration of Individual Devices>

5-1. Configuration of Skin Measurement Instrument 2

Figure 15:
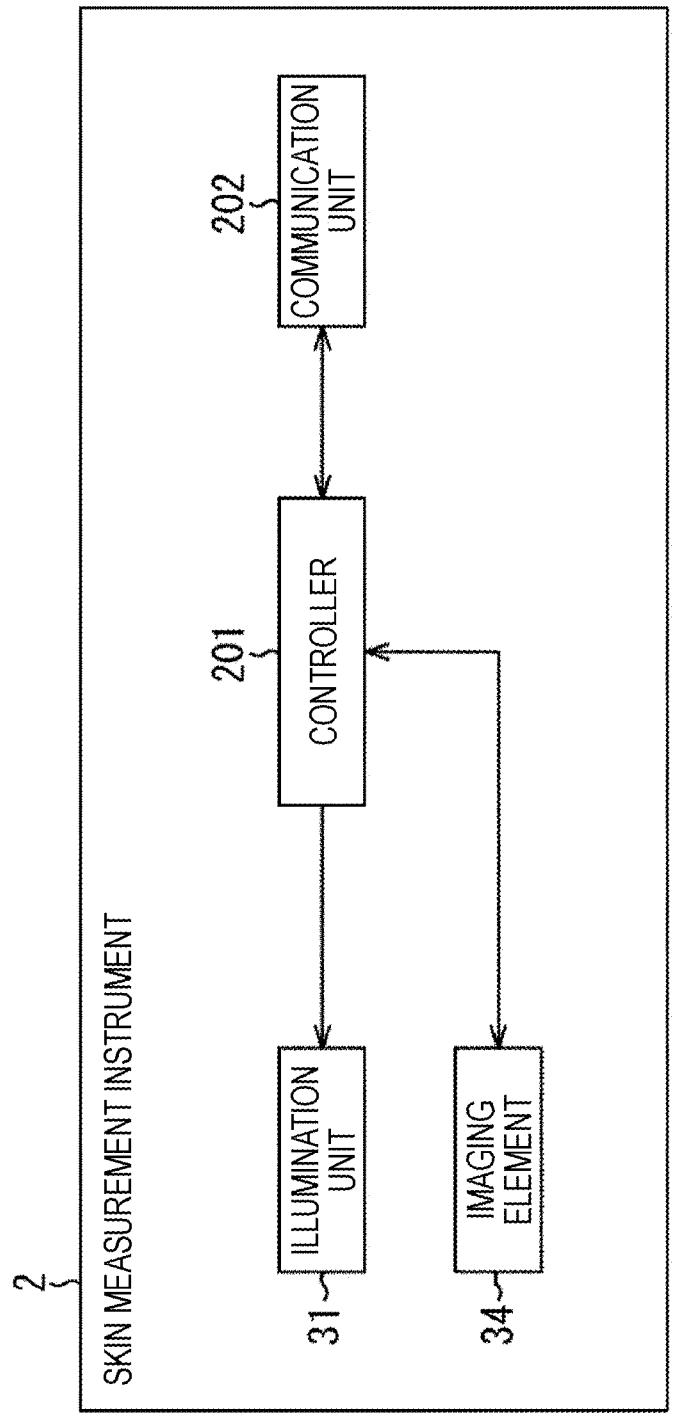
FIG. 15 is a block diagram illustrating an exemplary configuration of a skin measurement instrument.

FIG. 15 is a block diagram illustrating an exemplary configuration of the skin measurement instrument 2. The configuration that is same as the configuration illustrated in FIG. 3 is provided with a same reference sign. Overlapping description will be appropriately omitted.

The skin measurement instrument 2 includes the illumination unit 31, the imaging element 34, a controller 201, and a communication unit 202.

When the skin image is photographed, the illumination unit 31 emits visible light toward the skin. Moreover, the illumination unit 31 emits light with a predetermined wavelength used for melanin measurement, or the like.

The imaging element 34 corresponds to an image element such as a complementary metal oxide semiconductor (CMOS) image sensor. The imaging element 34 detects reflected light of the light emitted by the illumination unit 31 and performs photoelectric conversion, or the like. The imaging element 34 outputs the skin image data obtained by execution the photoelectric conversion, or the like, to the controller 201.

The controller 201 communicates with the information processing terminal 1 via the communication unit 202 and controls individual components of the skin measurement instrument 2 in accordance with the control of the information processing terminal 1, for example. The controller 201 transmits the skin image data supplied from the imaging element 34, from the communication unit 202 to the information processing terminal 1.

The communication unit 202 is a communication module according to a predetermined standard such as a wireless LAN. The communication unit 202 communicates with the information processing terminal 1. The communication unit 202 outputs information transmitted from the information processing terminal 1, to the controller 201, and transmits the information supplied from the controller 201, to the information processing terminal 1.

5-2. Configuration of Information Processing Apparatus

Figure 16:
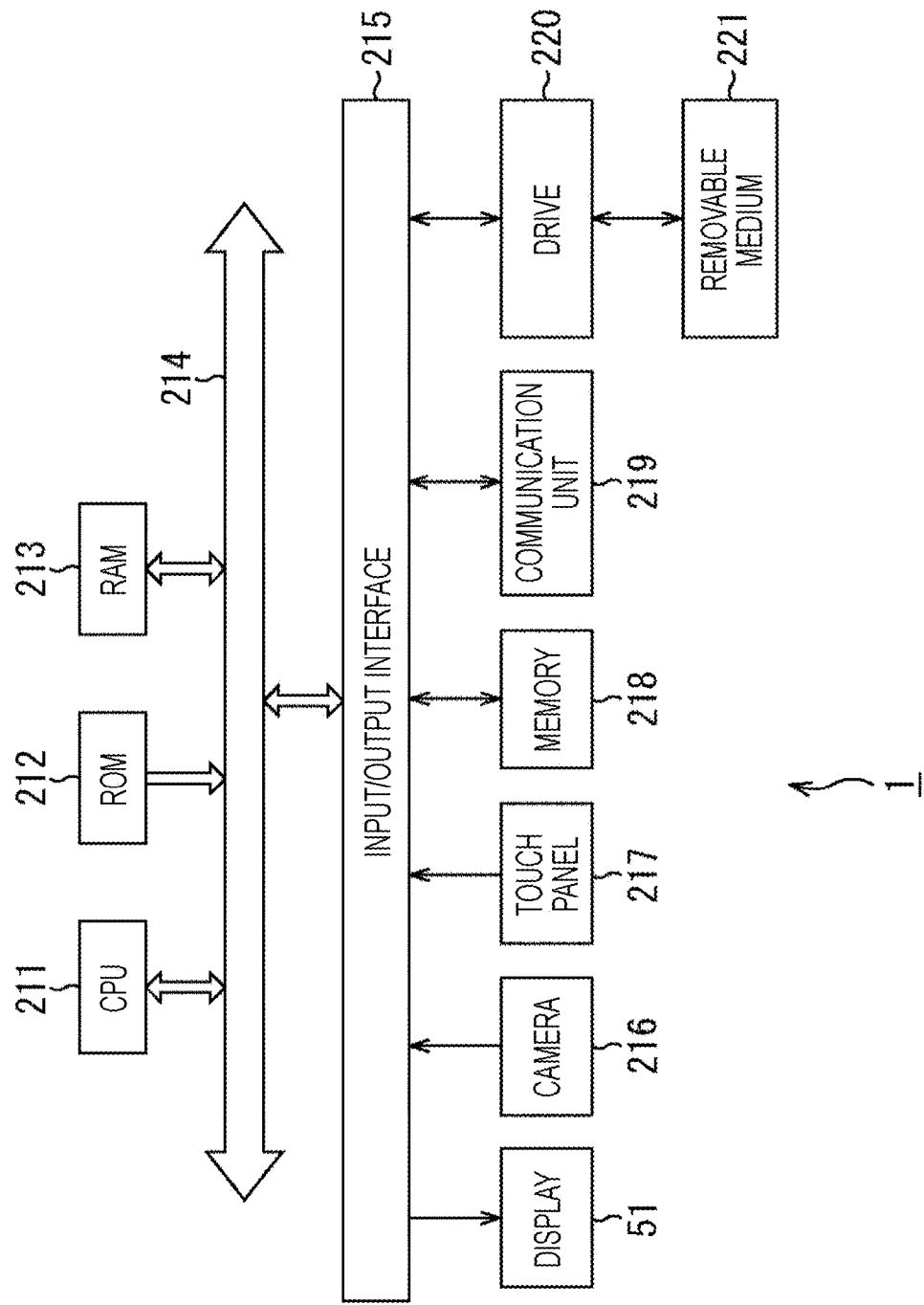
FIG. 16 is a block diagram illustrating an exemplary hardware configuration of an information processing terminal.

FIG. 16 is a block diagram illustrating an exemplary hardware configuration of the information processing terminal 1.

A central processing unit (CPU) 211, a read only memory (ROM) 212, and a random access memory (RAM) 213 are connected with each other via a bus 214.

Further, an input/output interface 215 is connected to the bus 214. The input/output interface 215 is connected with the display 51, a camera 216, a touch panel 217, a memory 218, a communication unit 219, and a drive 220.

The touch panel 217 is provided to be stacked on the display 51. The touch panel 217 detects user's operation and outputs the information representing the operation content to the CPU 211.

The memory 218 is configured with a flash memory, or the like. The memory 218 records various types of information such as information representing skin condition analysis results transmitted from the analysis server 3. The information recorded in the memory 218 is appropriately read by the CPU 211.

The communication unit 219 is a communication module according to a predetermined standard such as a wireless LAN. The communication unit 219 communicates with the skin measurement instrument 2. Moreover, the communication unit 219 is connected to a relay apparatus 4A, and communicates with the analysis server 3, or the like, connected via the network 4.

The drive 220 reads the data recorded in a removable medium 221 and records data onto the removable medium 221. The removable medium 221 is a recording medium such as a memory card attached onto a slot provided on the information processing terminal 1, and a USB memory attached onto a terminal on the information processing terminal 1.

Figure 17:
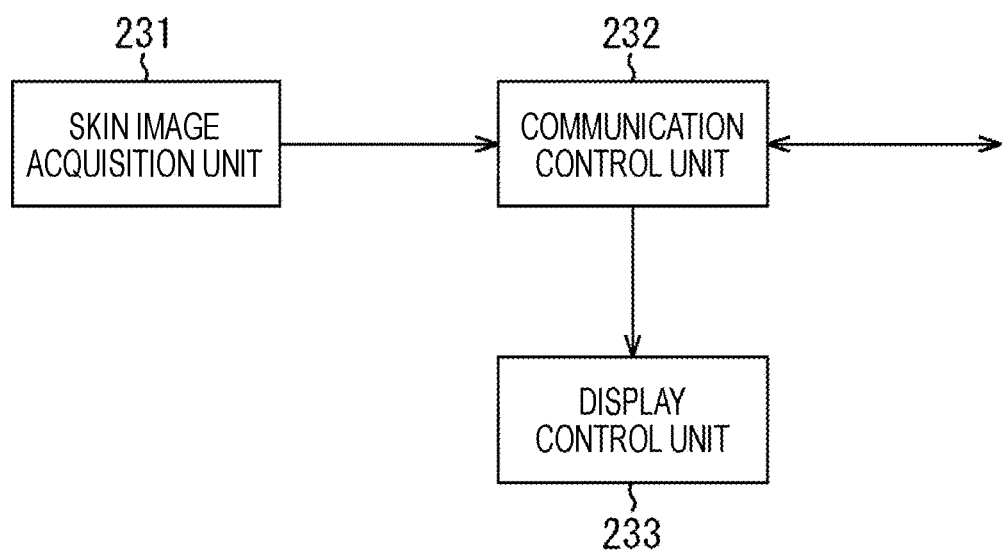
FIG. 17 is a block diagram illustrating an exemplary functional configuration of the information processing terminal.

FIG. 17 is a block diagram illustrating an exemplary functional configuration of the information processing terminal 1.

At least a portion of a functional unit illustrated in FIG. 17 is implemented by execution of a predetermined program by the CPU 211 in FIG. 16.

As illustrated in FIG. 17, the information processing terminal 1 includes a skin image acquisition unit 231, a communication control unit 232, and a display control unit 233.

At the time of measuring skin conditions, the skin image acquisition unit 231 obtains a skin image photographed by the skin measurement instrument 2 and received on the communication unit 219. For example, a plurality of skin images photographed with different wavelengths is obtained for one measurement position. The skin image acquisition unit 231 outputs the obtained skin image to the communication control unit 232.

The communication control unit 232 controls the communication unit 219 and transmits the skin image supplied from the skin image acquisition unit 231, to the analysis server 3. Moreover, the communication control unit 232 receives information representing the analysis result transmitted from the analysis server 3. The information representing the analysis result includes overall scores, scores for each of the measurement positions, comment information, and the analysis result display image for each of the items of "overall determination", "texture", "pore", "spot", "color tone", and "memo". The communication control unit 232 outputs information representing received analysis result, to the display control unit 233.

On the basis of the information supplied from the communication control unit 232, the display control unit 233 displays a measurement result display screen on the display 51 and presents skin condition analysis results to the user. Moreover, the display control unit 233 switches the display of the measurement result display screen in accordance with user's operation.

5-3. Configuration of the Analysis Server 3

Figure 18:
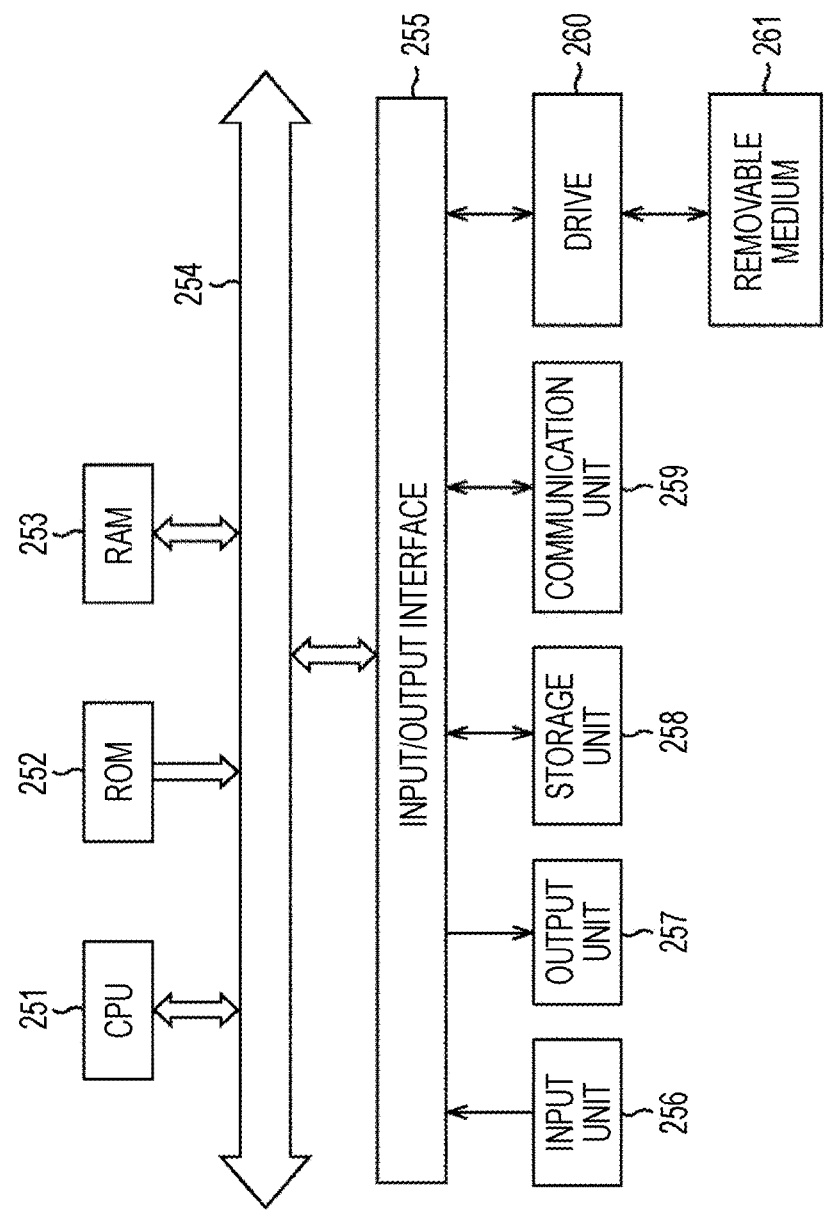
FIG. 18 is a block diagram illustrating an exemplary hardware configuration of an analysis server.

FIG. 18 is a block diagram illustrating an exemplary hardware configuration of the analysis server 3.

The CPU 251, the ROM 252, and the RAM 253 are connected with each other via a bus 254. Further, an input/output interface 255 is connected to the bus 254.

The input/output interface 255 is connected with an input unit 256 such as a keyboard and a mouse, and with an output unit 257 such as a display. Moreover, the input/output interface 255 is connected with a storage unit 258 such as a hard disk, and with a communication unit 259 configured to communicate with various devices such as the information processing terminal 1, via the network 4.

The input/output interface 255 is also connected with a drive 260. The drive 260 reads the data recorded in a removable medium 261 and records data onto the removable medium 261.

Figure 19:
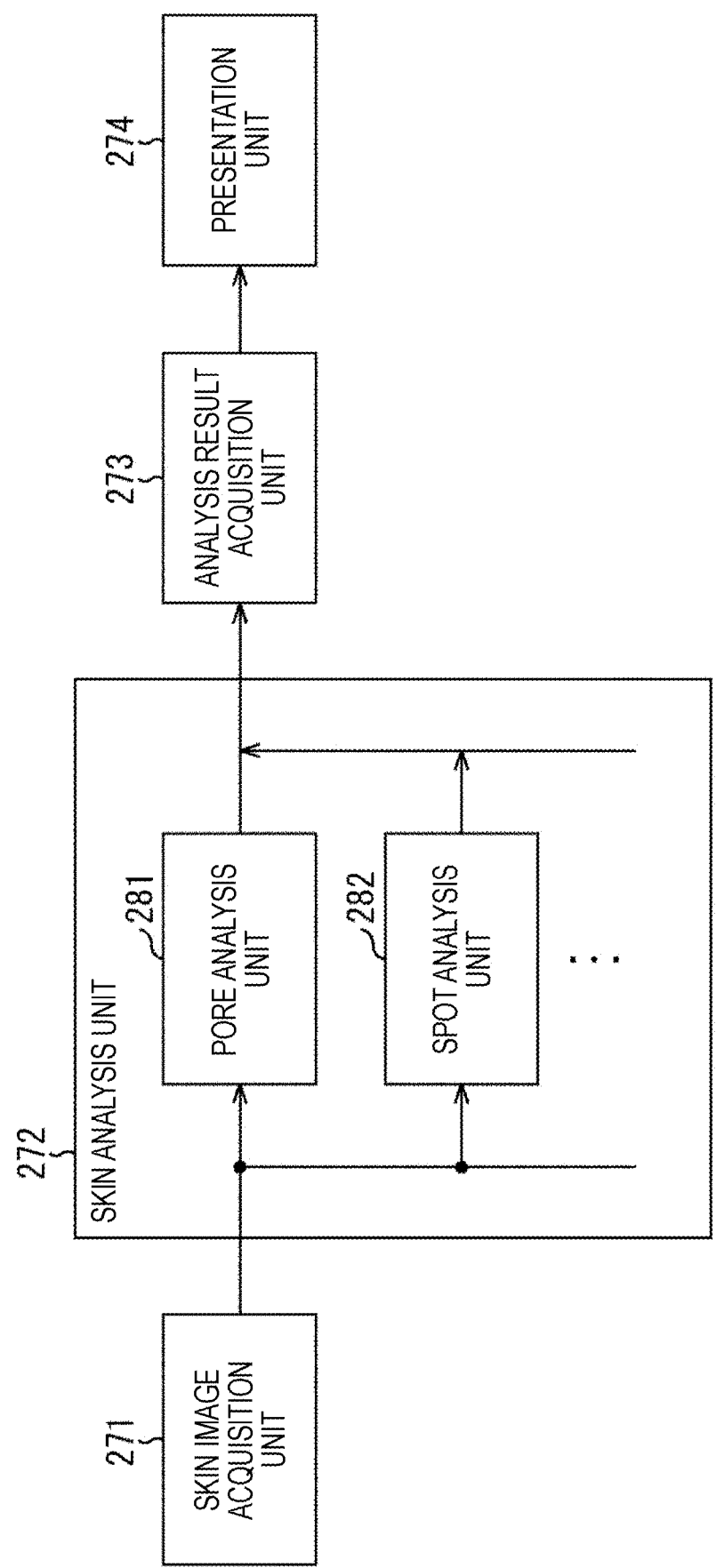
FIG. 19 is a block diagram illustrating an exemplary functional configuration of the analysis server.

FIG. 19 is a block diagram illustrating an exemplary functional configuration of the analysis server 3.

At least a portion of a functional unit illustrated in FIG. 19 is implemented by execution of a predetermined program by the CPU 251 in FIG. 18.

As illustrated in FIG. 19, the analysis server 3 includes a skin image acquisition unit 271, a skin analysis unit 272, an analysis result acquisition unit 273, and a presentation unit 274. The skin analysis unit 272 includes a pore analysis unit 281 and a spot analysis unit 282.

The skin image acquisition unit 271 controls the communication unit 259 and obtains a skin image transmitted from the information processing terminal 1. The skin image acquisition unit 271 outputs the obtained skin image to each of components of the skin analysis unit 272.

The pore analysis unit 281 of the skin analysis unit 272 performs image processing on the skin image supplied from the skin image acquisition unit 271 and analyzes the pore condition. The pore analysis unit 281 outputs, for example, information representing the pore opening condition and information representing the pore blackhead condition as information representing pore analysis results.

The spot analysis unit 282 performs image processing on the skin image supplied from the skin image acquisition unit 271 and analyzes the spot condition. The spot analysis unit 282 outputs, for example, information representing the reddish spot condition and information representing the melanin spot condition as the information representing spot analysis results.

The skin analysis unit 272 further includes various analysis units such as an analysis unit that analyzes the skin texture and an analysis unit that analyzes the color tone.

The analysis result acquisition unit 273 obtains information representing the analysis result output from each of the components of the skin analysis unit 272. The analysis result acquisition unit 273 outputs the obtained information to the presentation unit 274 at a predetermined timing.

The presentation unit 274 generates information representing the skin condition analysis results on the basis of the information supplied from the analysis result acquisition unit 273. The presentation unit 274 transmits the generated information to the information processing terminal 1 by controlling the communication unit 259, and presents the skin condition analysis results to the user.

About Spot Analysis Unit 282

Figure 20:
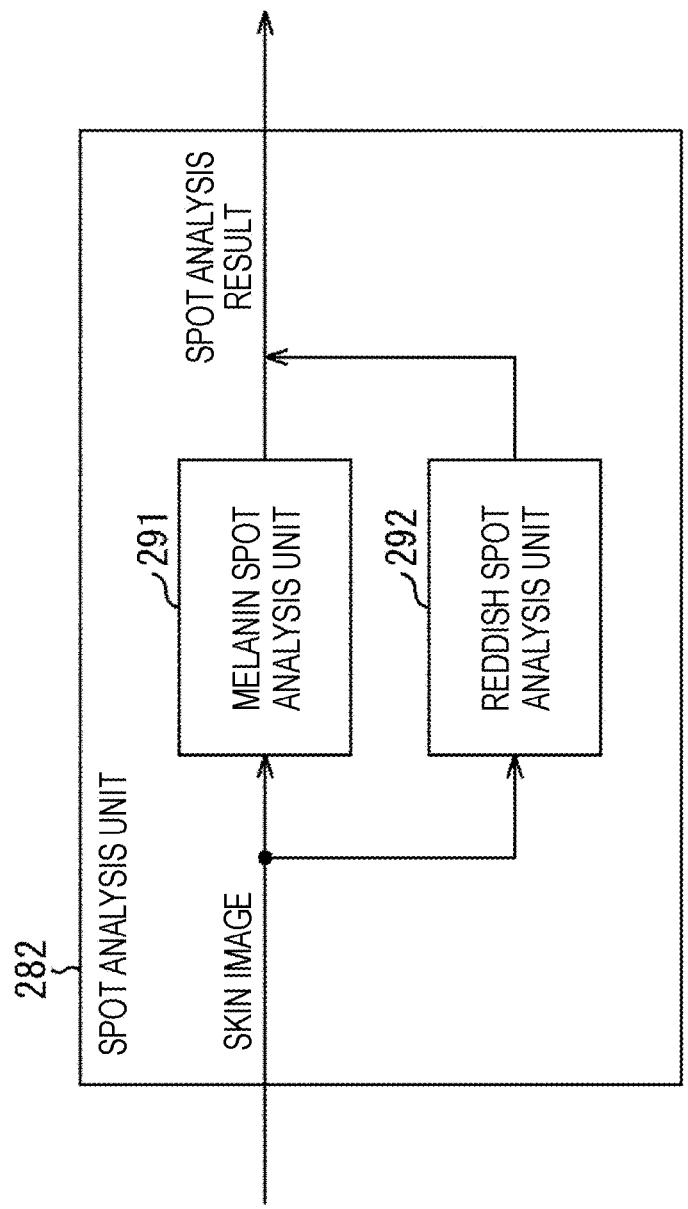
FIG. 20 is a block diagram illustrating an exemplary configuration of a spot analysis unit.

FIG. 20 is a block diagram illustrating an exemplary configuration of the spot analysis unit 282.

The spot analysis unit 282 includes a melanin spot analysis unit 291 and a reddish spot analysis unit 292. The skin image output from the skin image acquisition unit 271 is input into each of the melanin spot analysis unit 291 and the reddish spot analysis unit 292.

The melanin spot analysis unit 291 performs image processing on the skin image, thereby analyzing the melanin spot conditions. The melanin spot analysis unit 291 outputs information representing an analysis result.

The reddish spot analysis unit 292 performs image processing on the skin image, thereby analyzing the reddish spot conditions. The reddish spot analysis unit 292 outputs information representing an analysis result.

Figure 21:
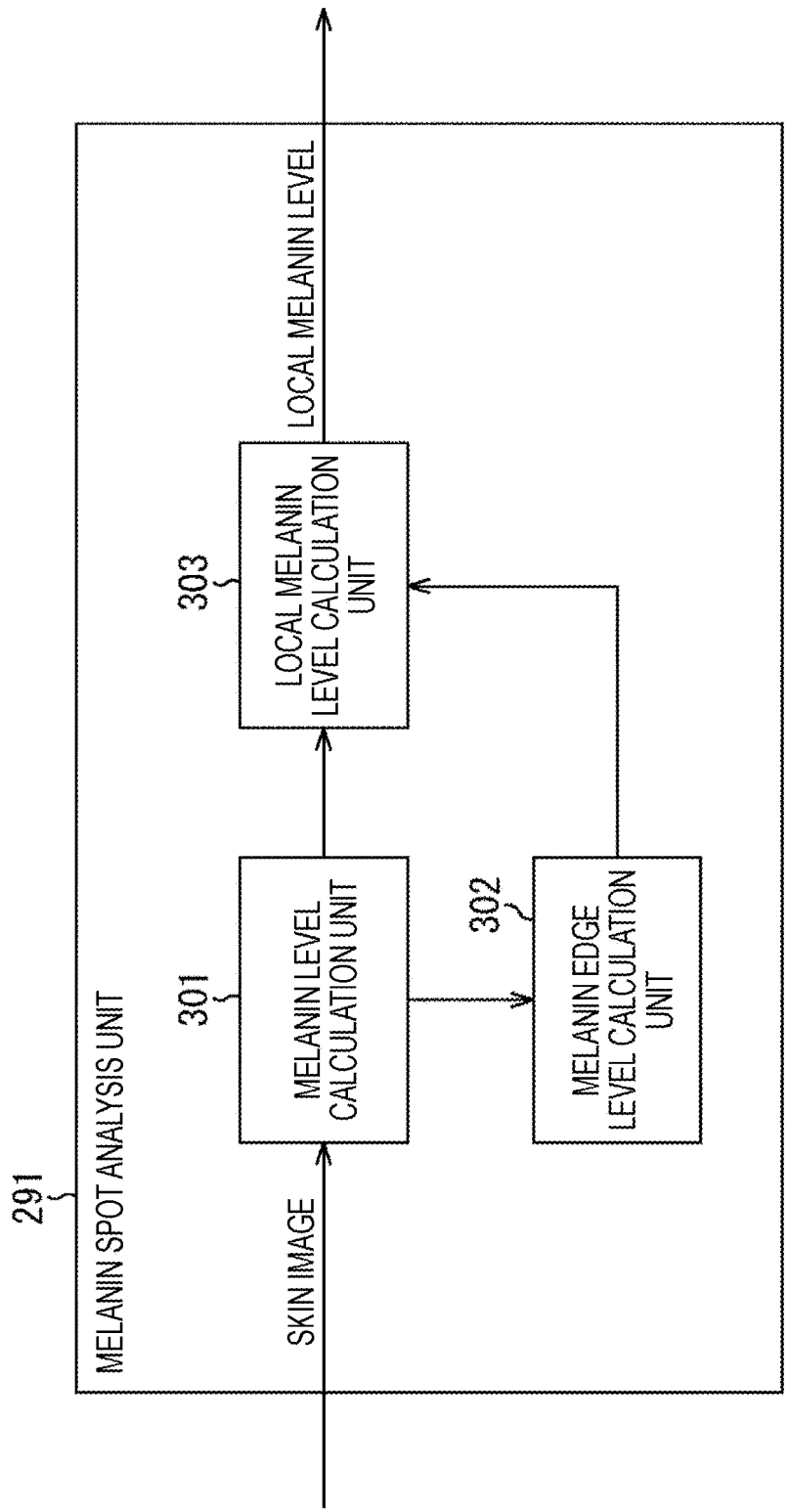
FIG. 21 is a block diagram illustrating an exemplary configuration of a melanin spot analysis unit in FIG. 20.

FIG. 21 is a block diagram illustrating an exemplary configuration of the melanin spot analysis unit 291 in FIG. 20.

The melanin spot analysis unit 291 includes a melanin level calculation unit 301, a melanin edge level calculation unit 302, and a local melanin level calculation unit 303. The melanin spot analysis unit 291 has a function of detecting a melanin component in the skin.

Figure 22:
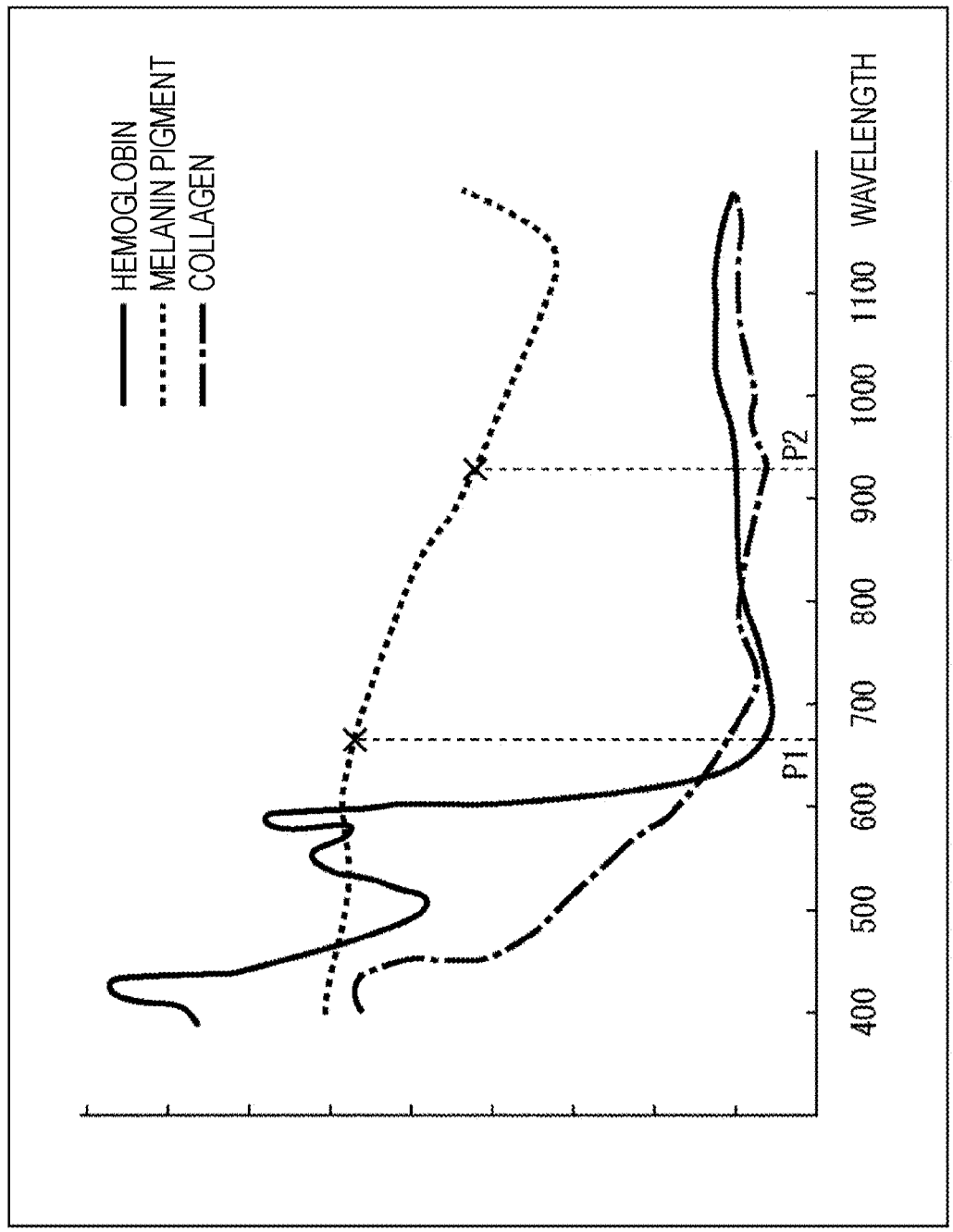
FIG. 22 is a diagram illustrating a light absorption characteristic of melanin.

The melanin level calculation unit 301 analyzes the skin image and obtains a melanin amount at each of positions (melanin component distribution). As illustrated in FIG. 22, melanin indicates a light absorption characteristic of a downward trend between a red wavelength zone indicated by a position P1 and a near infrared wavelength zone indicated by a position P2.

Using the melanin light absorption characteristic, the melanin level calculation unit 301 obtains a melanin amount $MX(x,y)$ on the basis of the skin image photographed under a red light source and the skin image photographed under a near infrared light source. The melanin amount $MX(x,y)$ is represented by the following Formula (1).

[Mathematical Formula 1]

$$MX(x,y) = A_{MAX}(\log(I_{IR}(x,y)) - (\log(I_R(x,y)) + B_{MX} \quad (1)$$

In Formula (1), $I_{IR}(x,y)$ represents a brightness (e.g. R pixel value) at a position (x,y) on the skin image photographed under the near infrared light source. $I_R(x,y)$ represents a brightness (e.g. R pixel value) at a position (x,y) on the skin image photographed under the red light source.

Figure 23:
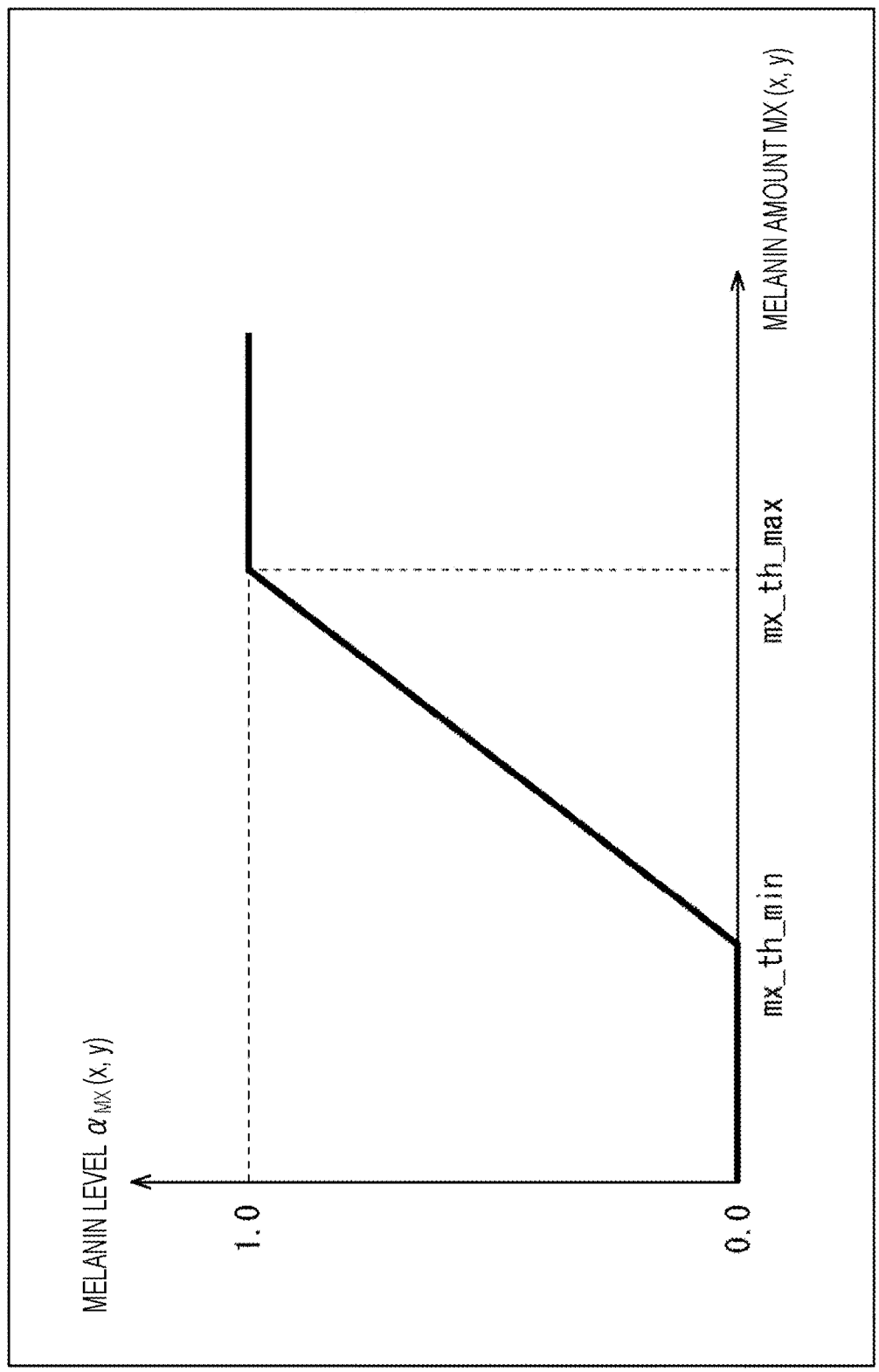
FIG. 23 is a diagram illustrating an exemplary normalization function.

Moreover, $A_{MX}$ and $B_{MX}$ are parameters for calculating the melanin amount. In accordance with the normalization function illustrated in FIG. 23, the melanin level calculation unit 301 adjusts the melanin distribution contrast by normalizing the melanin amount MX (x,y) at each of the positions to the value in the range [0,1]. The melanin level calculation unit 301 outputs information representing the melanin amount MX(x,y), to a melanin edge level calculation unit 302, and outputs the value representing the melanin amount at each of the positions after normalization, to the local melanin level calculation unit 303, as a melanin level $\alpha_{MX}(x,y)$.

The melanin edge level calculation unit 302 calculates the melanin edge level on the basis of the melanin amount MX(x,y) at each of the positions obtained by the melanin level calculation unit 301. The melanin edge level is a value representing the locality of melanin.

The melanin edge level calculation unit 302 creates an edge image that is an image representing a difference between the melanin amount at each of the positions and the melanin amount around the position. Exemplary methods for creating the edge image include a method using a Sobel filter. The Sobel filter is a filter used in detection of the outline. The value at each of the positions on the edge image is defined as mx_edge(x,y).

Figure 24:
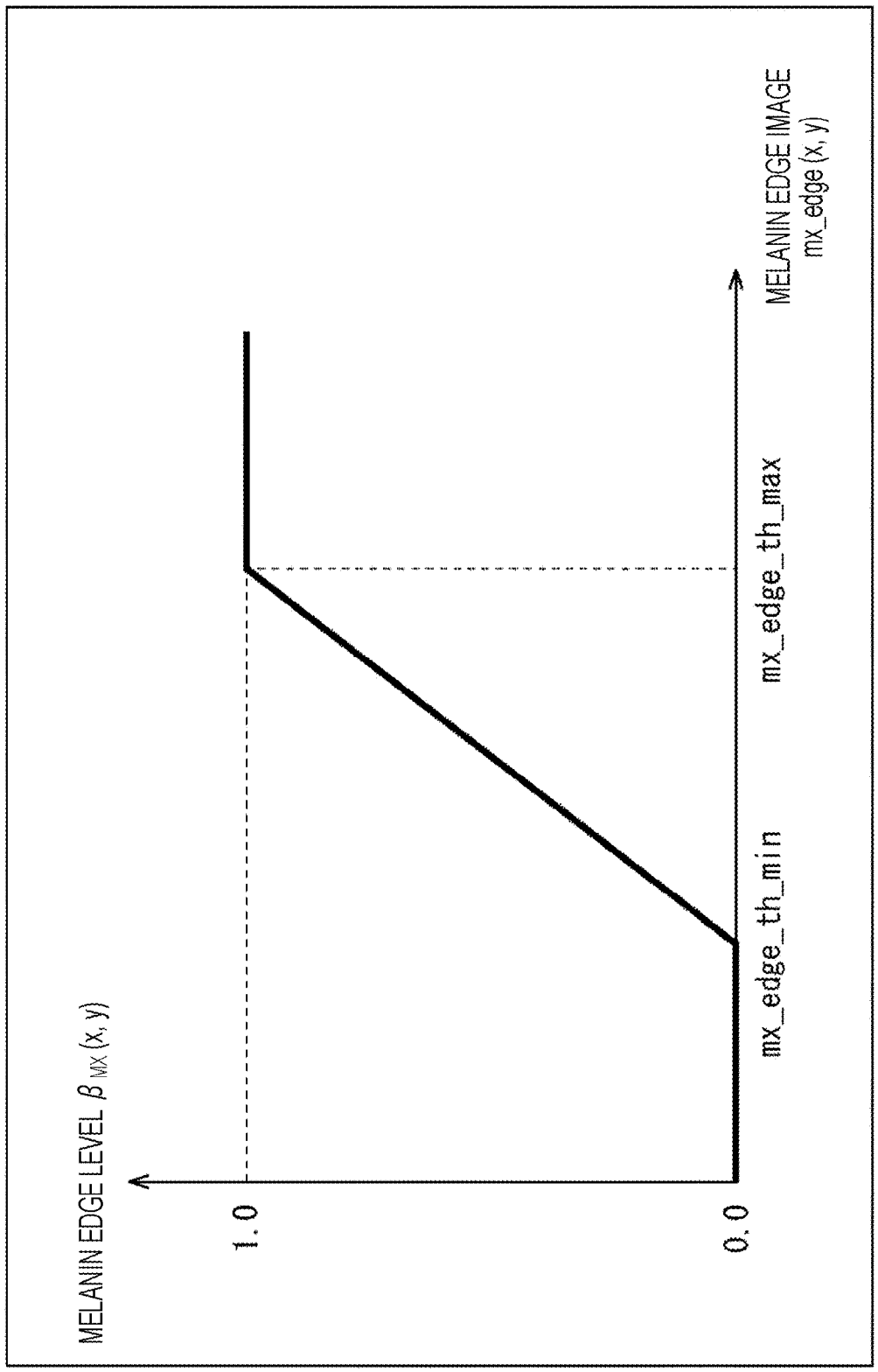
FIG. 24 is a diagram illustrating another exemplary normalization function.

The value mx_edge(x,y) takes a higher value in a portion where the melanin amount is locally higher or locally lower than the surrounding portions. In accordance with the normalization function in FIG. 24, the melanin edge level calculation unit 302 normalizes mx_edge(x,y) to the value in the range of [0.1], and outputs the value after normalization to the local melanin level calculation unit 303 as a melanin edge level $\beta_{MX}(x,y)$.

The local melanin level calculation unit 303 calculates a local melanin level $\gamma_{MX}(x,y)$ by multiplying the melanin level $\alpha_{MX}(x,y)$ obtained by the melanin level calculation unit 301 with the melanin edge level $\beta_{MX}(x,y)$ obtained by the melanin edge level calculation unit 302. The local melanin level $\gamma_{MX}(x,y)$ has a higher value at a position where the melanin level is higher than the surrounding portions. The local melanin level calculation unit 303 outputs the information representing the local melanin level $\gamma_{MX}(x,y)$ as a melanin spot analysis result.

Note that, in a case where a high melanin level region is relatively large, there might be a case where solely the local melanin level surrounding the region indicates a high value while the local melanin level at the center portion indicates a low value. To prevent this, the local melanin level calculation unit 303 performs binarization processing, for example, of filling a detected closed region with surrounding values.

Figure 25:
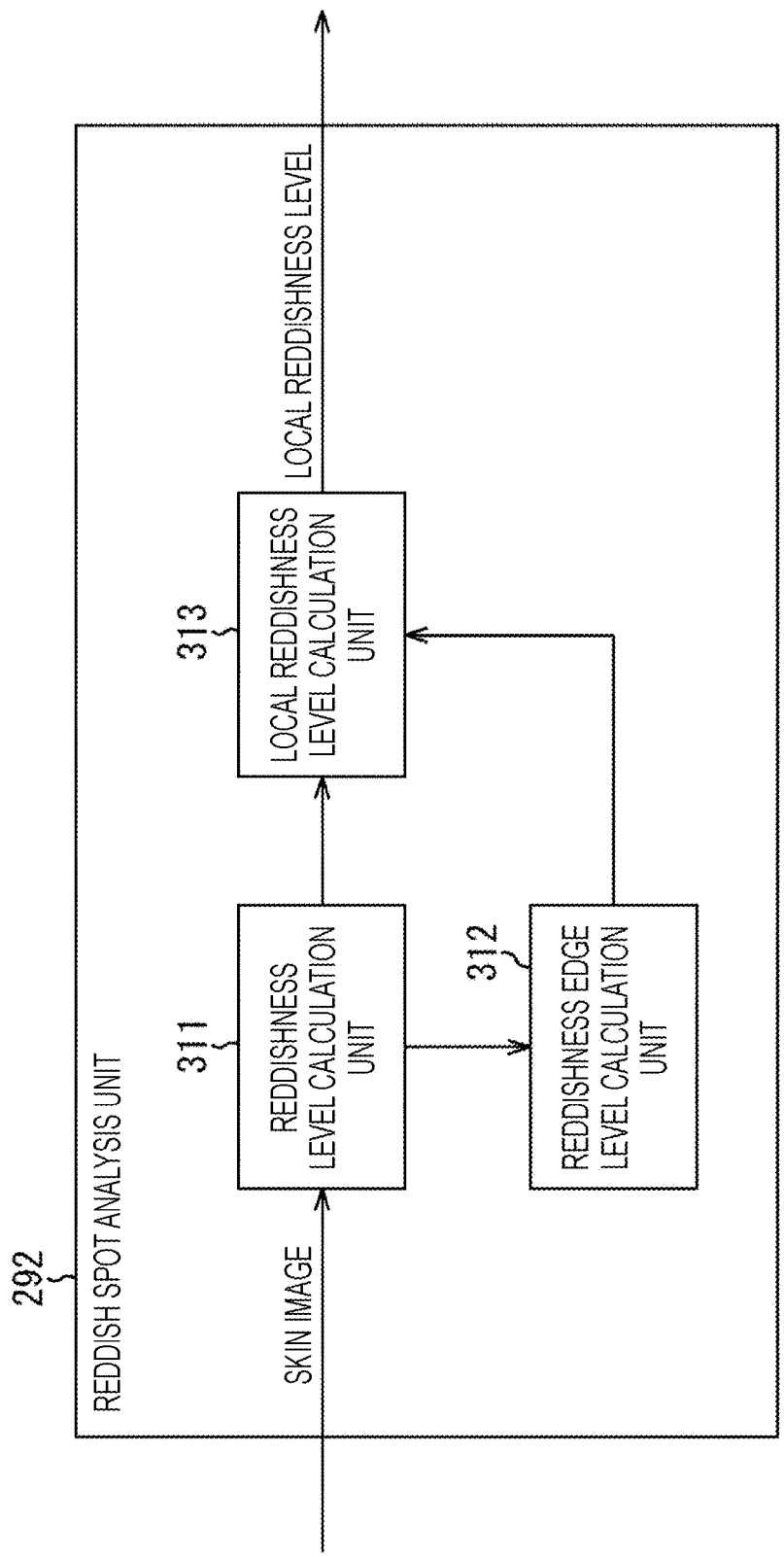
FIG. 25 is a block diagram illustrating an exemplary configuration of a reddish spot analysis unit in FIG. 20.

FIG. 25 is a block diagram illustrating an exemplary configuration of the reddish spot analysis unit 292 in FIG. 20.

The reddish spot analysis unit 292 includes a reddishness level calculation unit 311, a reddishness edge level calculation unit 312, and a local reddishness level calculation unit 313. The reddish spot analysis unit 292 has a function of detecting a hemoglobin component (reddish component) of the skin.

Figure 26:
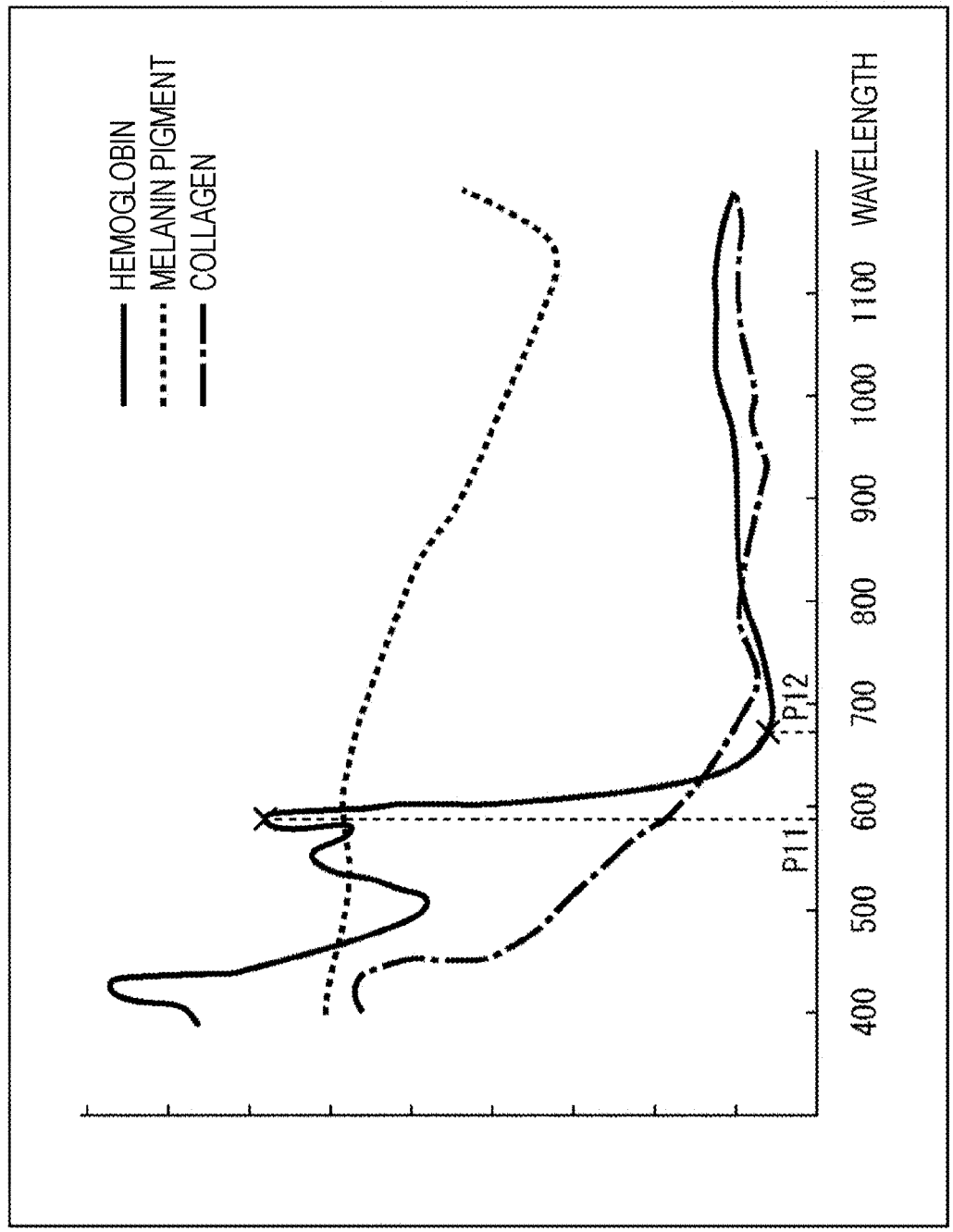
FIG. 26 is a diagram illustrating a light absorption characteristic of hemoglobin.

The reddishness level calculation unit 311 analyzes the skin image and obtains the hemoglobin amount at each of positions (hemoglobin component distribution). As illustrated in FIG. 26, hemoglobin indicates a light absorption characteristic of a downward trend between a green wavelength zone indicated by a position P11 and a red wavelength zone indicated by a position P12.

Using a light absorption characteristic of hemoglobin, the reddishness level calculation unit 311 obtains a reddishness amount EX(x,y) on the basis of the skin image photographed under the green light source and the skin image photographed under the red light source. The reddishness amount EX(x,y) is represented by the following Formula (2).

[Mathematical Formula 2]

$$EX(x,y)=A_{EX}(\log(I_R(x,y))-\log(I_G(x,y)))+B_{EX} \qquad (2)$$

In Formula (2), $I_R(x,y)$ represents a brightness (e.g. R pixel value) at a position (x,y) on the skin image photographed under the red light source. $I_G(x,y)$ represents a brightness (e.g. G pixel value) at a position (x,y) on the skin image photographed under the green light source.

Figure 27:
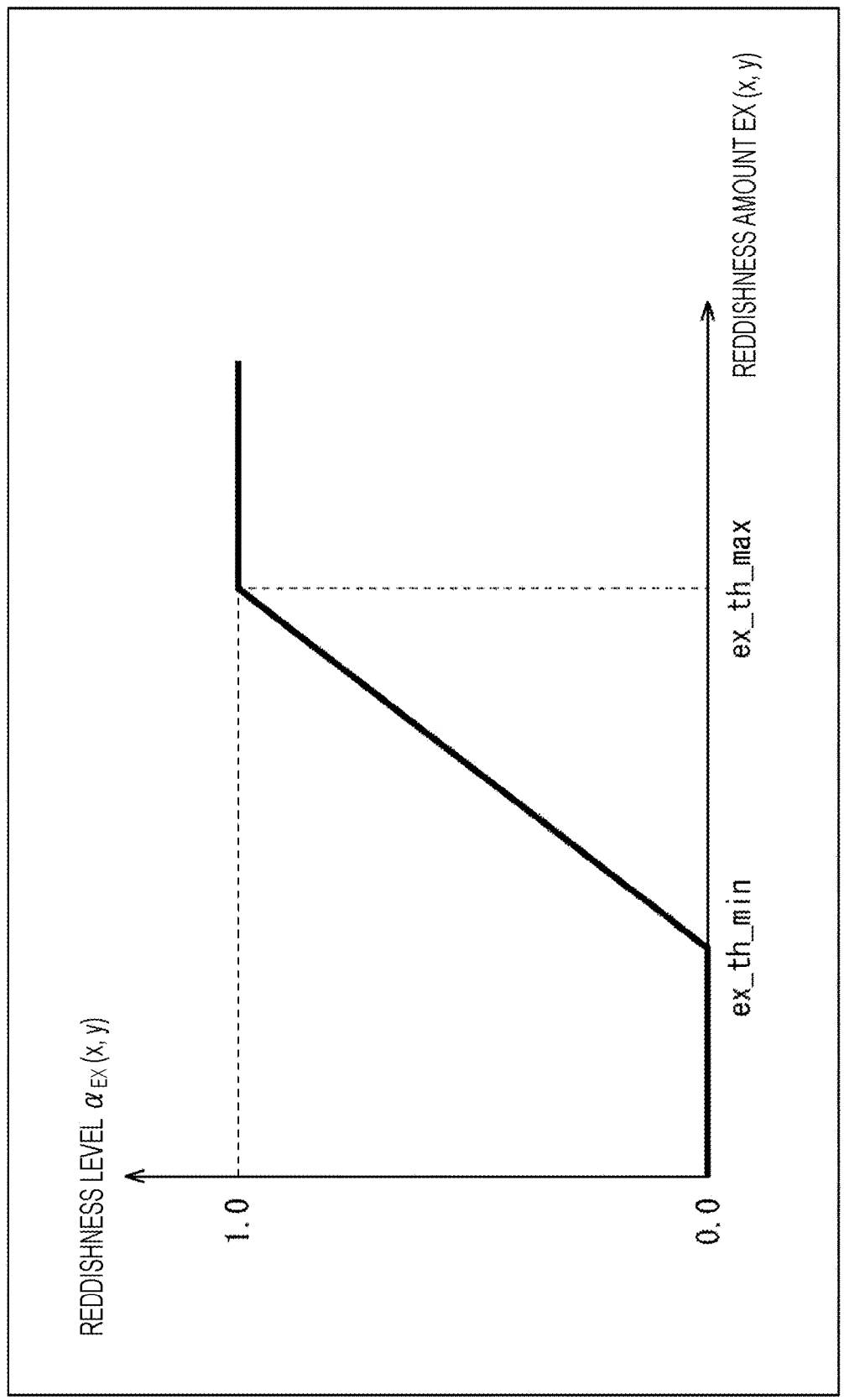
FIG. 27 is a diagram illustrating an exemplary normalization function.

Moreover, $A_{EX}$ and $B_{EX}$ are parameters for calculating the reddishness amount. In accordance with the normalization function illustrated in FIG. 27, the reddishness level calculation unit 311 adjusts the reddishness amount contrast by normalizing the reddishness amount EX(x,y) at each of the positions to the value in the range [0,1]. The reddishness level calculation unit 311 outputs information representing the reddishness amount EX(x,y), to the reddishness edge level calculation unit 312, and outputs the value representing the reddishness amount at each of the positions after normalization, to the local reddishness level calculation unit 313, as a reddishness level $\alpha_{EX}(x,y)$.

The reddishness edge level calculation unit 312 calculates a reddishness edge level on the basis of the reddishness amount EX(x,y) at each of the positions obtained by the reddishness level calculation unit 311. The reddishness edge level is a value representing the locality of reddishness amount.

The reddishness edge level calculation unit 312 creates an edge image that is an image representing a difference between the reddishness amount at each of the positions and the reddishness amount around the position. Exemplary methods for creating the edge image include a method using a Sobel filter. The value at each of the positions on the edge image is defined as ex_edge(x,y).

Figure 28:
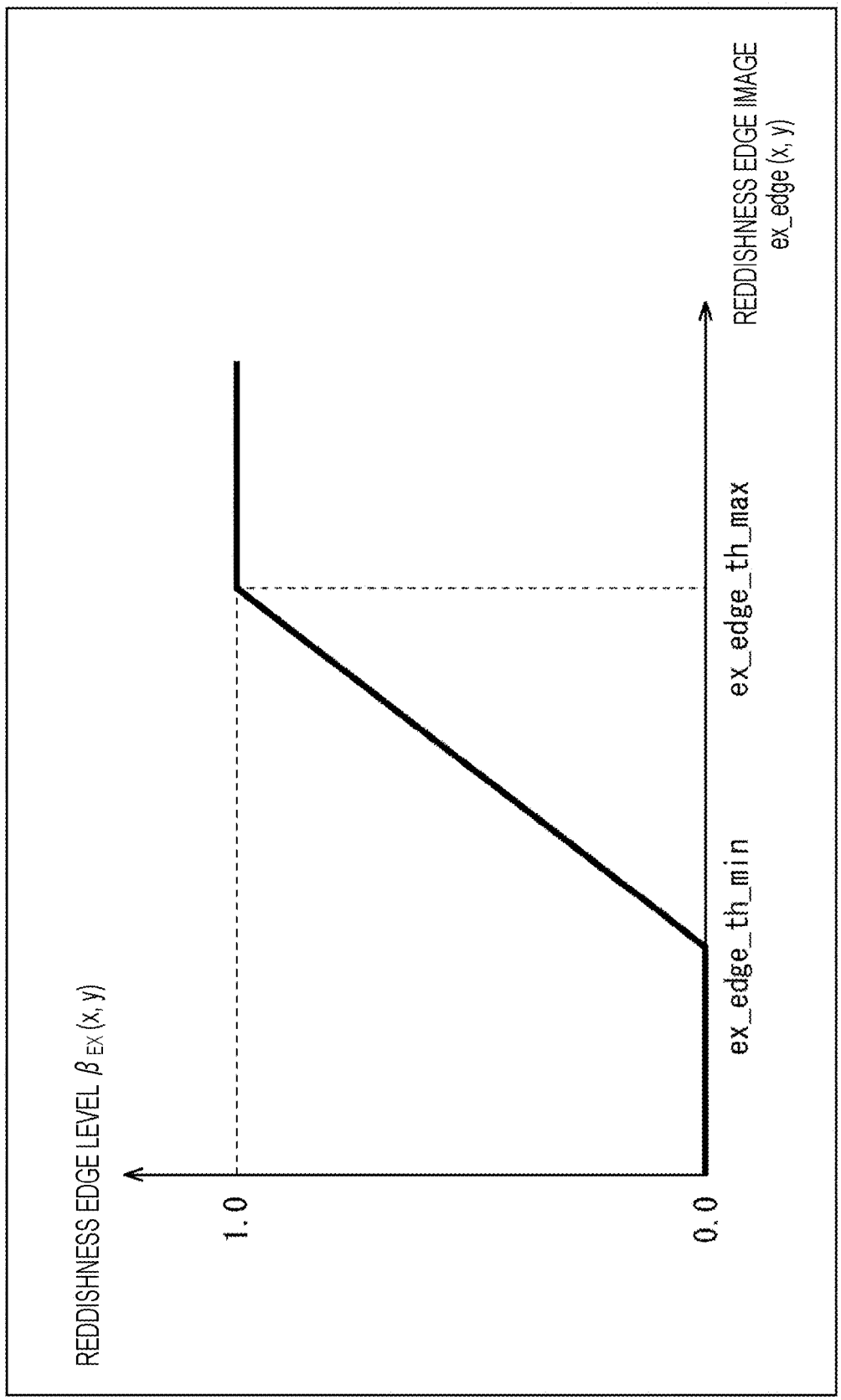
FIG. 28 is a diagram illustrating another exemplary normalization function.

The value ex_edge(x,y) takes a higher value in a portion where the reddishness amount is locally higher or locally lower than the surrounding portions. In accordance with the normalization function in FIG. 28, the reddishness edge level calculation unit 312 normalizes ex_edge(x,y) to the value in the range of [0.1], and outputs the value after normalization to the local reddishness level calculation unit 313 as a reddishness edge level $\beta_{EX}(x,y)$.

The local reddishness level calculation unit 313 calculates a local reddishness level $\gamma_{EX}(x,y)$ by multiplying the reddishness level $\alpha_{EX}(x,y)$ obtained by the reddishness level calculation unit 311 with the reddishness edge level $\beta_{EX}(x,y)$ obtained by the reddishness edge level calculation unit 312. The local reddishness level $\gamma_{EX}(x,y)$ has a higher value at a position where the reddishness level is higher than the surrounding portions. The local reddishness level calculation unit 313 outputs the information representing the local reddishness level $\gamma_{EX}(x,y)$ as a reddishness spot analysis result.

Note that, in a case where a high reddishness level region is relatively large, there might be a case where solely the local reddishness level surrounding the region indicates a high value while the local reddishness level at the center portion indicates a low value. To prevent this, the local reddishness level calculation unit 313 performs binarization processing, for example, of filling a detected closed region with surrounding values.

In this manner, the spot analysis unit 282 calculates distribution of each of the melanin component and the hemoglobin component. Moreover, the spot analysis unit 282 specifies a position where the amount of each of the components is locally high and generates information representing the amount of each of the components in the region including the specified position, as a spot analysis result.

Methods for analyzing the reddish spot and the melanin spot are not limited to the above-described methods. For example, it is also possible to simply detect the color of each of the regions on the skin image photographed by emitting visible light, specify the region of the color close to red as a reddish spot region and specify the region of the color close to brown as a melanin spot region.

About the Pore Analysis Unit 281

Figure 29:
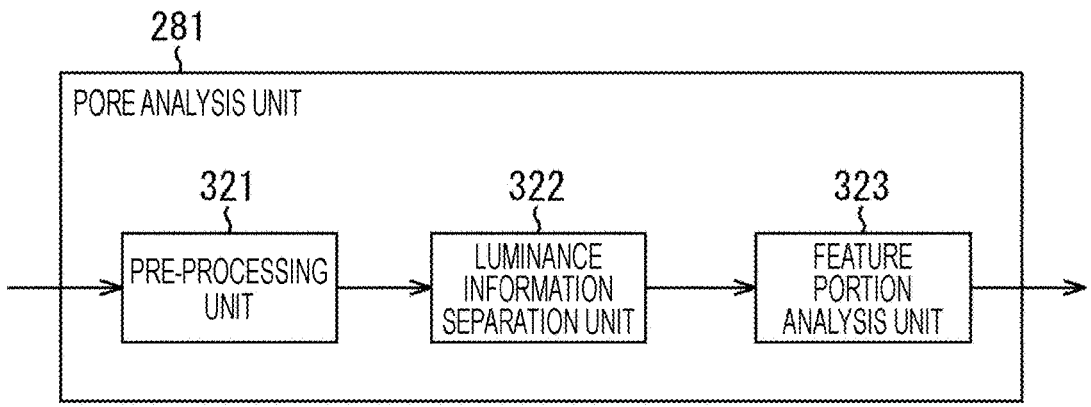
FIG. 29 is a block diagram illustrating an exemplary configuration of a pore analysis unit.

FIG. 29 is a block diagram illustrating an exemplary configuration of the pore analysis unit 281 in FIG. 19.

The pore analysis unit 281 includes a pre-processing unit 321, a luminance information separation unit 322, and a feature portion analysis unit 323. The skin image output from the skin image acquisition unit 271 is input into the pre-processing unit 321.

The pre-processing unit 321 performs processing as pre-processing, such as noise reduction, shading correction, and contrast enhancement, onto the skin image. The pre-processing unit 321 outputs the pre-processed skin image data to the luminance information separation unit 322.

The luminance information separation unit 322 separates luminance information on the pre-processed skin image into global luminance information and local luminance information. The global luminance information is information indicating an illumination component included in the image, and skin structure components. Moreover, the local luminance information is information indicating a fine pattern such as texture of the skin. Separation of the luminance information is performed by using, for example, a low pass filter. The luminance information separation unit 322 outputs the global luminance information together with the skin image, to the feature portion analysis unit 323.

The feature portion analysis unit 323 calculates feature data from the skin image and analyzes a feature portion of the skin on the basis of the calculated feature data.

Figure 30:
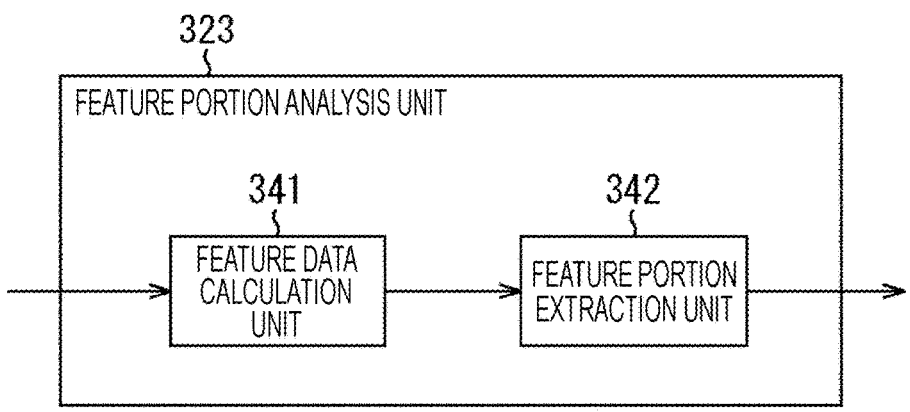
FIG. 30 is a block diagram illustrating an exemplary configuration of a feature portion analysis unit in FIG. 29.

FIG. 30 is a block diagram illustrating an exemplary configuration of the feature portion analysis unit 323.

The feature portion analysis unit 323 includes a feature data calculation unit 341 and a feature portion extraction unit 342.

The feature data calculation unit 341 calculates feature data on the basis of the global luminance information separated by the luminance information separation unit 322. The feature data calculation unit 341 calculates, for example, the polarity regarding the tone of the skin image, the scale representing a pixel region having similar pixel values different from the surrounding portions, and the intensity representing the signal difference between the image region having similar pixel values and the surrounding portions, as the feature data.

Calculation of the feature data uses techniques such as a speeded up robust feature (SURF) and a scale invariant feature transform (SIFT). In a case of using the SURF, for example, the feature data calculation unit 341 searches for a point where the matrix value in the Hessian matrix as the feature point in the image becomes maximum, by changing a standard deviation σ of the Gaussian function.

The feature portion extraction unit 342 extracts a portion of pore as a feature portion on the basis of the feature data obtained by the feature data calculation unit 341. For example, the feature portion extraction unit 342 extracts a portion of the feature point where the Laplacian representing polarity regarding the tone of the skin image becomes "1". When the Laplacian is "1", it means a black pixel is surrounded by white pixels.

Moreover, the feature portion extraction unit 342 extracts a portion where scales of approximately 0.1 mm 0.3 mm are calculated among the portion of the feature point extracted on the basis of the polarity, as a pore portion. The typical pore size is approximately 0.1 mm to 0.3 mm.

The feature portion extraction unit 342 outputs the information on a central position of the feature point extracted as the pore portion, as information on the pore position. Moreover, the feature portion extraction unit 342 outputs the information on a scale of the feature point extracted as the pore portion, as information representing the pore opening degree. Furthermore, the feature portion extraction unit 342 outputs the information on the intensity of the feature point extracted as the pore portion, as information representing the pore blackhead degree.

Information representing the pore position, the pore opening degree, and the pore blackhead degree, output from the feature portion extraction unit 342, is supplied to the analysis result acquisition unit 273 as the information representing pore condition analysis results.

Note that pore condition analysis as described above is disclosed in JP 2012-180861 from the applicant. Methods for analyzing pore conditions are not limited to the above-described methods.

<6. Operation of Individual Devices>

Next, processing performed by the above-configured information processing terminal 1 and the analysis server 3 will be described.

First, skin image transmission processing on the information processing terminal 1 will be described with reference to the flowchart in FIG. 31.

Figure 31:
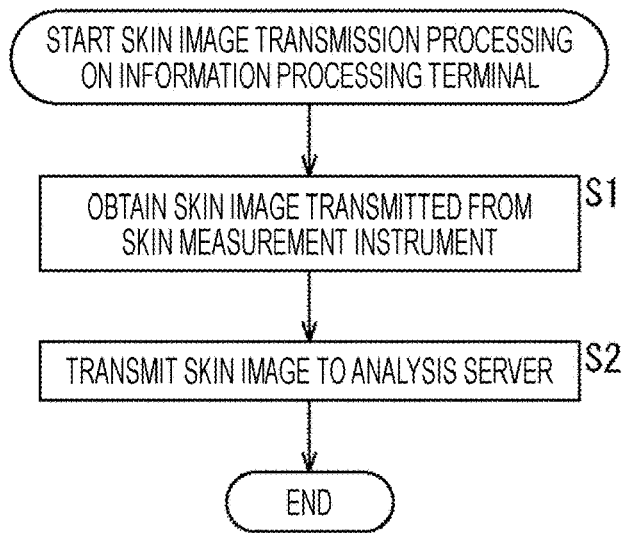
FIG. 31 is a flowchart illustrating skin image transmission processing on the information processing terminal.

The processing in FIG. 31 is started when the user photographs one's own skin using the skin measurement instrument 2 and when the skin image obtained by photographing is transmitted from the skin measurement instrument 2.

In step S1, the skin image acquisition unit 231 of the information processing terminal 1 controls the communication unit 219, and obtains the skin image transmitted from the skin measurement instrument 2.

In step S2, the communication control unit 232 controls the communication unit 219, and transmits the skin image obtained by the skin image acquisition unit 231 to the analysis server 3. Thereafter, the information processing terminal 1 waits until any feedback to the skin condition analysis results comes.

Next, skin condition analysis processing of the analysis server 3 will be described with reference to the flowchart in FIG. 32.

Figure 32:
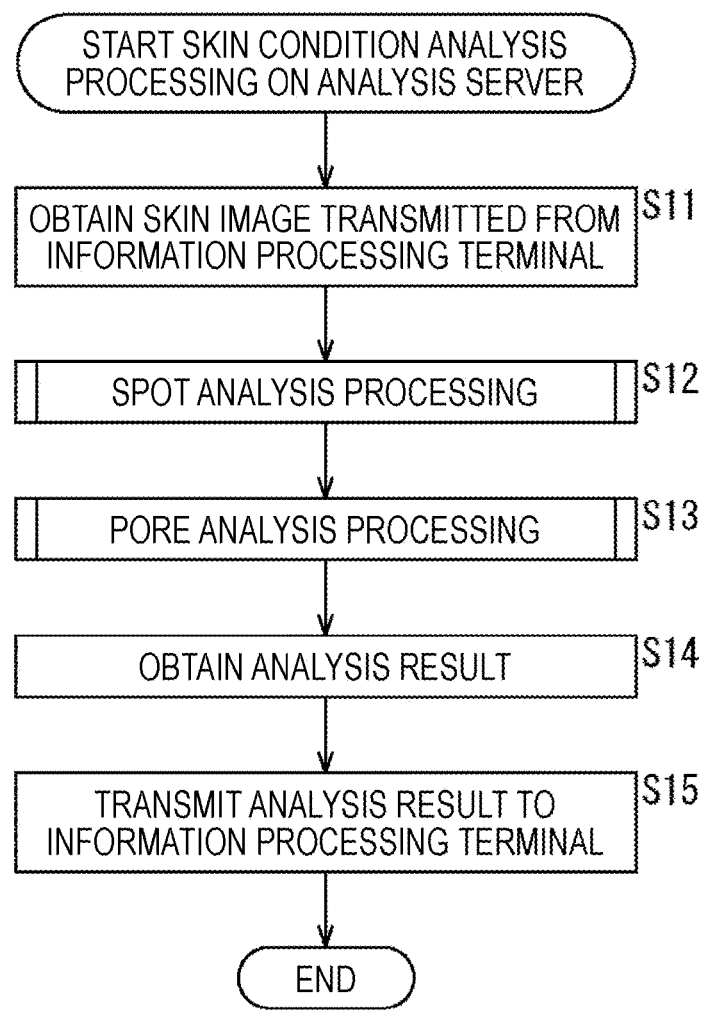
FIG. 32 is a flowchart illustrating skin condition analysis processing on the analysis server.

Processing in FIG. 32 is started when the skin image photographed by using the skin measurement instrument 2 is transmitted from the information processing terminal 1.

In step S11, the skin image acquisition unit 271 controls the communication unit 259, and obtains the skin image transmitted from the information processing terminal 1.

In step S12, the spot analysis unit 282 of the skin analysis unit 272 performs spot analysis processing. By the spot analysis processing, the spot condition is analyzed on the basis of the skin image. The spot analysis processing will be described later with reference to the flowchart in FIG. 33.

In step S13, the pore analysis unit 281 performs pore analysis processing. With the pore analysis processing, the pore condition is analyzed on the basis of the skin image. The pore analysis processing will be described later with reference to the flowchart in FIG. 34.

In step S14, the analysis result acquisition unit 273 obtains, as a result of spot condition analysis result, information representing the reddish spot condition and information representing the melanin spot condition, obtained by spot analysis processing. Moreover, the analysis result acquisition unit 273 obtains, as a result of pore condition analysis result, information representing the pore opening condition and information representing the pore blackhead condition, obtained by pore analysis processing.

The skin analysis unit 272 also performs texture condition analysis, color tone condition analysis, or the like. The analysis result acquisition unit 273 also obtains information representing a texture condition analysis result and a color tone analysis result.

In step S15, the presentation unit 274 generates information representing skin condition analysis results on the basis of the information obtained by the analysis result acquisition unit 273 and transmits the generated information to the information processing terminal 1. Thereafter, processing of the analysis server 3 is finished.

Figure 33:
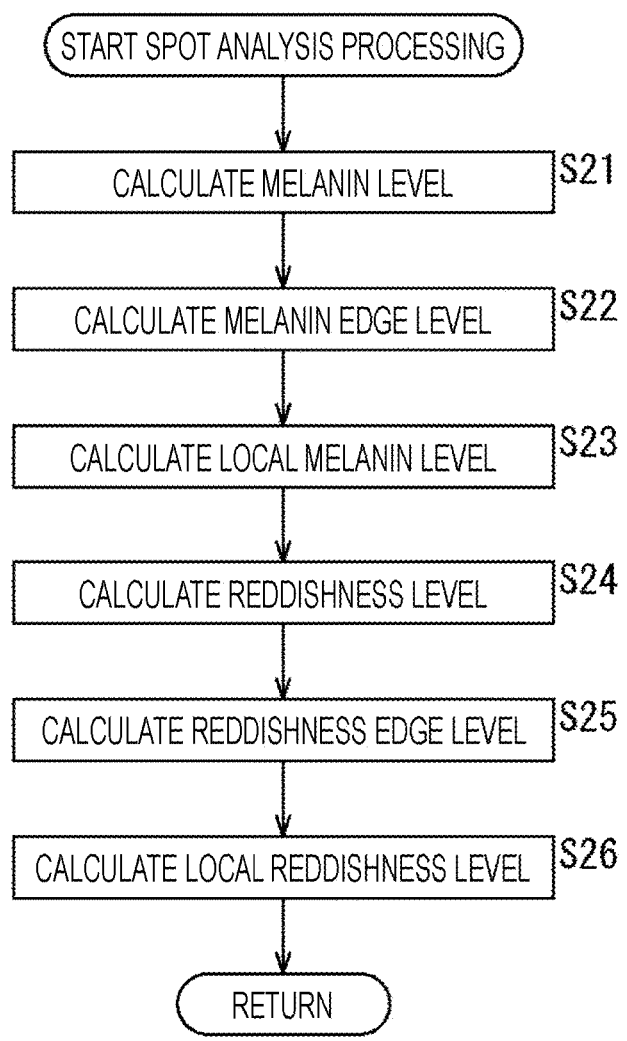
FIG. 33 is a flowchart illustrating spot analysis processing performed in step S12 in FIG. 32.

Next, the spot analysis processing performed in step S12 in FIG. 32 will be described with reference to the flowchart in FIG. 33.

In step S21, the melanin level calculation unit 301 of the melanin spot analysis unit 291 calculates the melanin amount on the basis of the skin image photographed under the red light source and the skin image photographed under the near infrared light source and normalizes the calculated melanin amount, thereby calculating the melanin level.

In step S22, the melanin edge level calculation unit 302 calculates the value representing the locality of the melanin amount by applying, for example, the melanin amount of each of the positions obtained by the melanin level calculation unit 301, to the Sobel filter, or the like. Moreover, the melanin edge level calculation unit 302 normalizes the calculated value, thereby calculating the melanin edge level.

In step S23, the local melanin level calculation unit 303 calculates a local melanin level by multiplying the melanin level obtained by the melanin level calculation unit 301 with the melanin edge level obtained by the melanin edge level calculation unit 302. The local melanin level calculation unit 303 outputs the information representing the local melanin level as a melanin spot analysis result.

In step S24, the reddishness level calculation unit 311 of the reddish spot analysis unit 292 calculates the reddishness level by calculating the reddishness amount on the basis of the skin image photographed under the green light source and the skin image photographed under the red light source, and by performing normalization.

In step S25, the reddishness edge level calculation unit 312 calculates the value representing locality of the reddishness amount by applying, for example, the reddishness amount of each of the positions obtained by the reddishness level calculation unit 311 to the Sobel filter. Moreover, the reddishness edge level calculation unit 312 normalizes the calculated value, thereby calculating the reddishness edge level.

In step S26, the local reddishness level calculation unit 313 calculates a local reddishness level by multiplying the reddishness level obtained by the reddishness level calculation unit 311 with the reddishness edge level obtained by the reddishness edge level calculation unit 312. The local reddishness level calculation unit 313 outputs the information representing the local reddishness level as a reddishness spot analysis result.

Thereafter, processing returns to step S12 in FIG. 32, and further processing is performed.

Next, pore analysis processing performed in step S13 in FIG. 32 will be described with reference to the flowchart in FIG. 34.

In step S31, the pre-processing unit 321 of the pore analysis unit 281 performs processing as pre-processing, such as noise reduction, shading correction, and contrast enhancement, onto the skin image.

In step S32, the luminance information separation unit 322 separates luminance information on the pre-processed skin image, into global luminance information and local luminance information. The luminance information separation unit 322 outputs the global luminance information together with the skin image, to the feature portion analysis unit 323.

In step S33, the feature data calculation unit 341 of the feature portion analysis unit 323 calculates feature data of each of the positions as a feature point, on the basis of the global luminance information separated by the luminance information separation unit 322.

In step S34, the feature portion extraction unit 342 performs feature portion extraction processing. The feature portion extraction processing extracts the pore portion as a feature portion. Thereafter, processing returns to step S13 in FIG. 32, and further processing is performed.

Next, feature portion extraction processing performed in step S34 in FIG. 34 will be described with reference to the flowchart in FIG. 35.

In step S41, the feature portion extraction unit 342 selects a predetermined feature point, and obtains the feature data of the selected feature point from among the feature data calculated by the feature data calculation unit 341. For example, the polarity regarding the tone of the skin image, the scale representing a pixel region having similar pixel values different from the surrounding portions, and the intensity representing the signal difference between the image region having similar pixel values and the surrounding portions, are obtained as the feature data.

In step S42, the feature portion extraction unit 342 determines whether the polarity of the selected feature point is a predetermined polarity. Herein, whether the Laplacian representing the polarity of the selected feature point is "1" is determined. As described above, when the Laplacian is "1", it means that the pixel of the selected feature point is a black pixel and that the black pixel is surrounded by white pixels.

In a case where it is determined in step S42 that the polarity of the selected feature point is not a predetermined polarity, that is, the Laplacian is not "1, processing proceeds to step S43.

In step S43, the feature portion extraction unit 342 selects a new feature point and obtains feature data of the selected feature point. Thereafter, processing returns to step S42 and similar processing is repeated.

In contrast, in a case where it is determined in step S42 that the polarity of the selected feature point is a predetermined polarity due to the fact that the Laplacian is "1", processing proceeds to step S44.

In step S44, the feature portion extraction unit 342 determines whether the scale of the selected feature point is a predetermined scale. Herein, it is determined whether the scale of the selected feature point is in a range of 0.1 mm to 0.3 mm, for example.

Note that, in a case where it is determined in step S42 that the polarity of the selected feature point is a predetermined polarity, processing in step S47 is performed together with the processing in step S44. As described later, processing in step S47 is processing of determining whether the intensity of the selected feature point is a predetermined intensity.

That is, both scale determination and intensity determination are performed onto the feature point determined as a feature point for the pore portion. This enables specifying four pore portions of wide opening with a blackhead, wide opening without any blackhead, no wide opening with a blackhead, and no wide opening without any blackhead.

In case where it is determined in step S44 that the scale of the selected feature point is a predetermined scale, the feature portion extraction unit 342 specifies, in step S45, the portion of the selected feature point as a feature portion that corresponds to the open pore. The open pore is, for example, a pore that has an opening degree of the smallest degree of the six degrees illustrated with reference to FIG. 8, or more.

In step S46, the feature portion extraction unit 342 determines whether extraction of the feature portion that corresponds to the open pore is completed. This determination determines whether determination has been performed toward all the feature points as to whether they are feature portions that correspond to open pores.

In a case where it is determined in step S46 that extraction of the feature portion that corresponds to the open pore is not completed, or determined in step S44 that the scale of the selected feature point is not the predetermined scale, the feature portion extraction unit 342 performs step S43 and further processing.

In step S47, the feature portion extraction unit 342 determines whether the intensity of the selected feature point is predetermined intensity. Processing in step S47 is performed in a case where the scale of the selected feature point is a predetermined scale.

In case where it is determined in step S47 that the intensity of the selected feature point is predetermined intensity, the feature portion extraction unit 342 specifies, in step S48, the portion of the selected feature point as a feature portion that corresponds to the blackhead pore. The blackhead pore is, for example, a pore that has a lowest blackhead degree or above, of the six degrees illustrated with reference to FIG. 9.

In step S49, the feature portion extraction unit 342 determines whether extraction of the feature portion that corresponds to the blackhead pore is completed. This determination determines whether determination has been performed toward all the feature points as to whether they are feature portions that correspond to blackhead pores.

In a case where it is determined in step S49 that extraction of the feature portion that corresponds to the blackhead pore is not completed, or determined in step S47 that the intensity of the selected feature point is not a predetermined intensity or above, the feature portion extraction unit 342 performs step S43 and further processing.

In a case where it is determined, in step S46, that extraction of the feature portion that corresponds to the open pore is completed, or determined, in step S49, that extraction of the feature portion that corresponds to the blackhead pore is completed, processing proceeds to step S50.

The feature portion extraction unit 342 determines, in step S50, whether extraction of the feature portion that corresponds to open pore and extraction of the feature portion that corresponds to blackhead pore are completed, and in a case where extraction is not completed, the feature portion extraction unit 342 performs step S43 and further processing.

Figure 34:
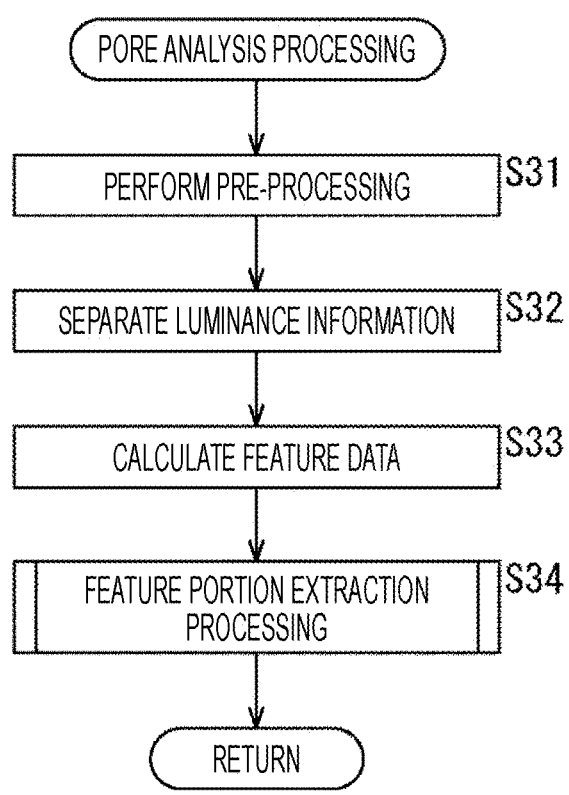
FIG. 34 is a flowchart illustrating pore analysis processing performed in step S13 in FIG. 32.
Figure 35:
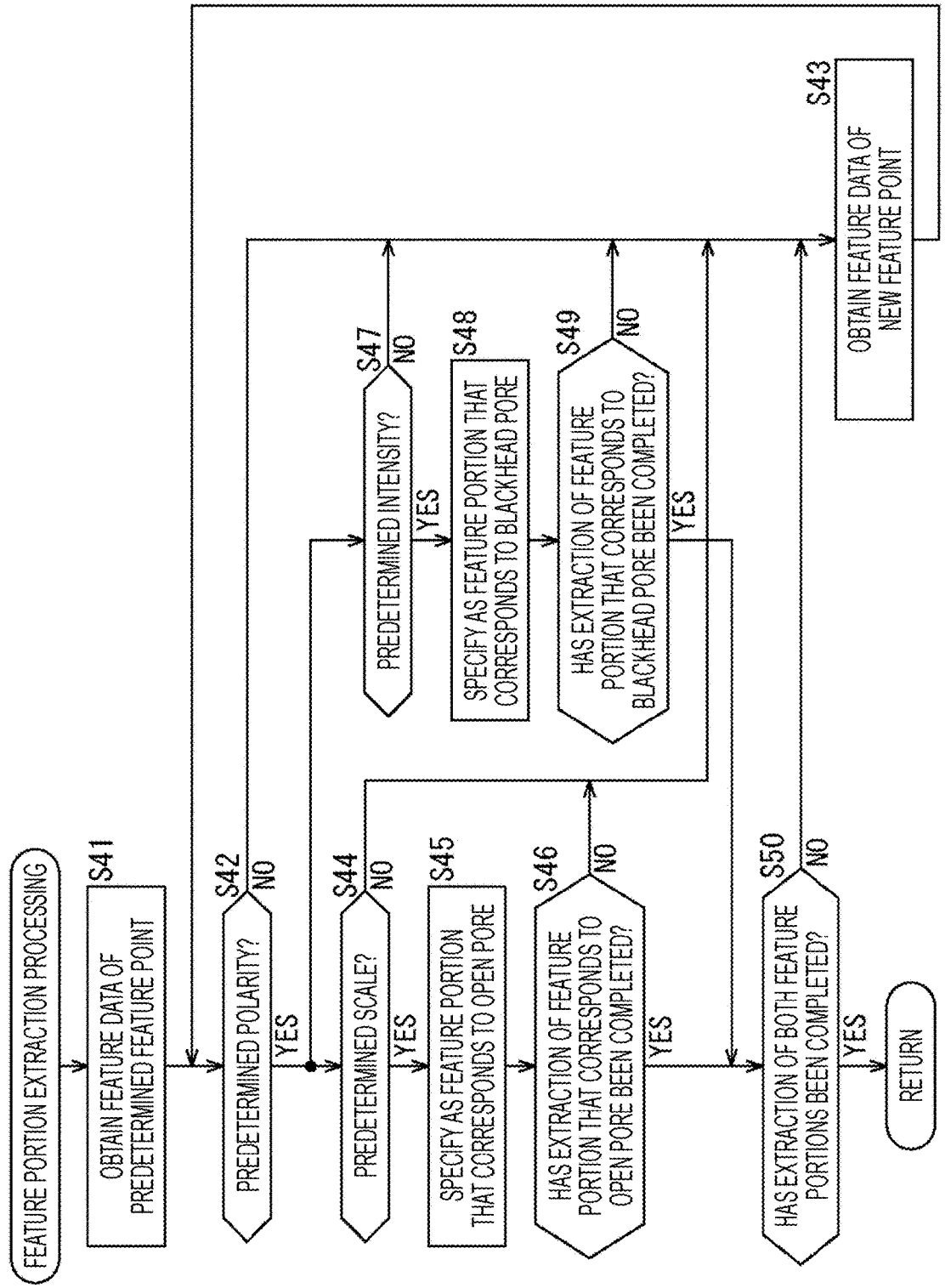
FIG. 35 is a flowchart illustrating feature portion extraction processing performed in step S34 in FIG. 34.

In a case where it is determined, in step S50, that extraction of the feature portion that corresponds to open pore and extraction of the feature portion that corresponds to blackhead pore are completed, processing returns to step S34 in FIG. 34 and further processing is performed.

Figure 36:
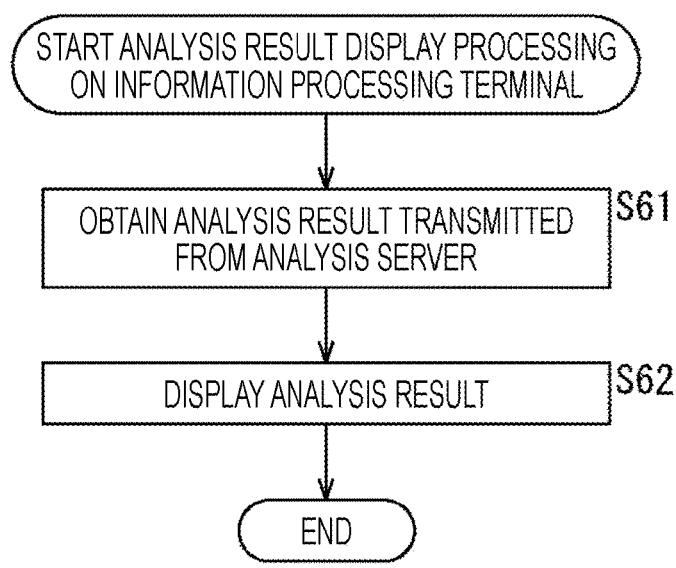
FIG. 36 is a flowchart illustrating analysis result display processing on the information processing terminal.

Next, analysis result display processing on the information processing terminal 1 will be described with reference to the flowchart in FIG. 36.

In step S61, the communication control unit 232 of the information processing terminal 1 receives and obtains information representing analysis results transmitted from the analysis server 3.

In step S62, the display control unit 233 displays the measurement result display screen illustrated with reference to FIG. 5 on the display 51 on the basis of the information obtained by the communication control unit 232. The display control unit 233 switches the display of the measurement result display screen in accordance with user's operation. In a case where closing of the measurement result display screen is instructed, processing is finished.

The above-described series of processing enables the user to check a plurality of types of analysis results regarding the skin conditions intuitively and easily.

Second Embodiment

Figure 37:
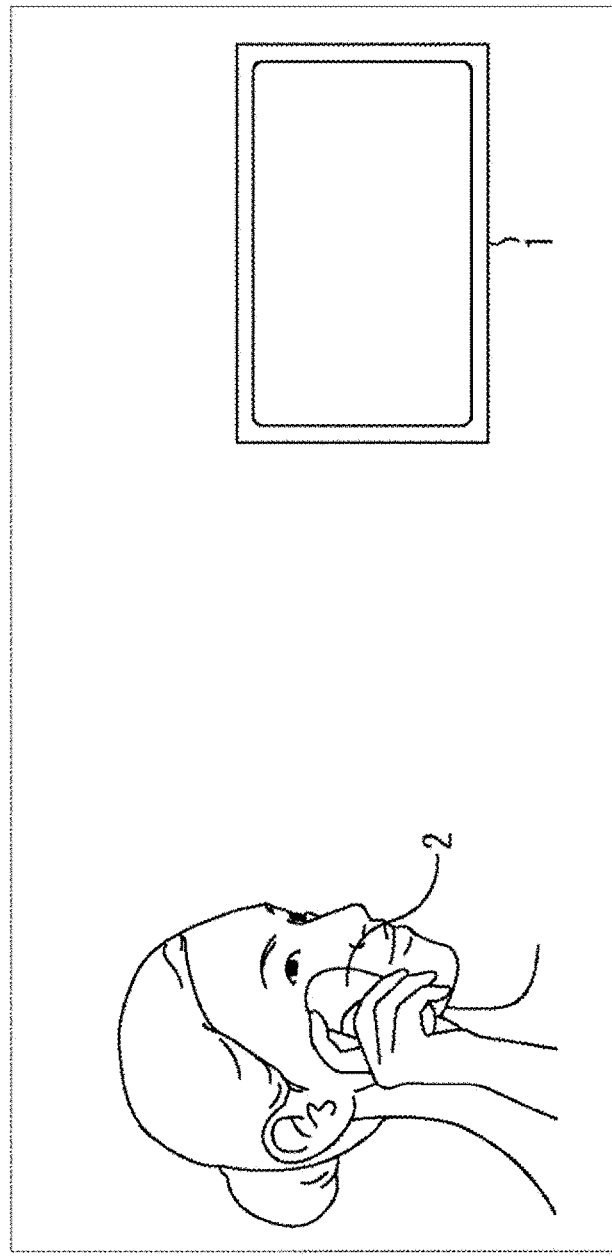
FIG. 37 is a diagram illustrating another exemplary configuration of the skin analysis system.

FIG. 37 is a diagram illustrating another exemplary configuration of the skin analysis system.

The skin analysis system in FIG. 37 includes the information processing terminal 1 and the skin measurement instrument 2.

The information processing terminal 1 obtains the skin image photographed by the skin measurement instrument 2 and analyzes user's skin condition on the basis of the obtained skin image. The information processing terminal 1 displays the measurement result display screen on the display 51 on the basis of the skin condition analysis results.

That is, the skin analysis system in FIG. 37 allows the information processing terminal 1 itself to perform skin condition analysis and to display the measurement result display screen. The information processing terminal 1 functions as an information processing apparatus configured to analyze skin conditions by performing image processing on the skin image. The information processing terminal 1 has a configuration same as the configuration illustrated in FIG. 19.

Modification Example

It is possible to allow a configuration same as the configuration illustrated in FIG. 19 to be provided in the skin measurement instrument 2. In this case, the skin measurement instrument 2 obtains a skin image by photographing and analyzes the skin condition by performing image processing on the obtained skin image. The skin measurement instrument 2 displays the analysis result display screen on the display 51 of the information processing terminal 1, for example, so as to present the skin condition analysis result to the user.

The above-described configuration is a case where the skin measurement instrument 2 is used as a device for photographing the skin image. Alternatively, however, it is also allowable to configure such that skin images can be photographed by the camera 216 mounted on the information processing terminal 1.

While the above-described configuration is a case where facial skin condition is analyzed, it is also allowable to use a portion such as a hand, arm, and foot, other than the face, as an analysis target skin portion.

About Program

A series of processing described above can be executed in hardware or with software. In a case where the series of processing is executed by software, a program constituting the software is installed onto a computer incorporated in dedicated hardware, a general-purpose computer, or the like.

The program to be installed is recorded and supplied in the removable medium 221 illustrated in FIG. 16, such as a compact disc read only memory (CD-ROM), a digital versatile disc (DVD), and a semiconductor memory. Moreover, the program may be supplied via a wired or wireless transmission medium including a local area network, the Internet, and digital satellite broadcasting. The program can be installed in the ROM 212 or the memory 218 beforehand.

Note that the program executed by the computer may be a program processed in a time series in an order described in the present description, or can be a program processed in required timing such as being called.

Note that, in the present description, the system represents a set of multiple constituents (apparatuses, modules (parts), or the like). In other words, all the constituents may be in a same housing but they do not have to be in the same housing. Accordingly, a plurality of apparatuses, housed in separate housings, connected via a network can be a system. An apparatus in which a plurality of modules is housed in one housing can also be a system.

Note that effects described herein are provided for purposes of exemplary illustration and are not intended to be limiting. Still other effects may also be contemplated.

Embodiments of the present technology are not limited to the above-described embodiments but can be modified in a variety of ways within a scope of the present technology.

For example, the present technology can be configured as a form of cloud computing in which one function is shared in cooperation for processing among a plurality of apparatuses via a network.

Moreover, each of steps described in the above flowcharts can be executed on one apparatus or shared by a plurality of apparatuses for processing.

Furthermore, in a case where one step includes a plurality of stages of processing, the plurality of stages of processing included in the one step can be executed on one apparatus or can be shared by a plurality of apparatuses.

Exemplary Combination of Configurations

The present technology can be configured as follows.

(1)

An information processing apparatus including:

an acquisition unit configured to obtain information representing a plurality of types of analysis results on skin conditions obtained by analyzing an image of a skin at a same position, and a presentation unit configured to simultaneously display, on a same image, a plurality of types of visualized information obtained from visualized representation of the plurality of types of analysis results.

(2)

The information processing apparatus according to the above-described (1), in which the presentation unit displays the visualized information on the image of the skin used for obtaining the analysis result.

(3)

The information processing apparatus according to the above-described (1) or (2), in which the presentation unit displays the visualized information representing the plurality of types of analysis results obtained by analyzing the image of the skin at a selected position, in accordance with the selection of the position of the skin.

(4)

The information processing apparatus according to any of the above-described (1) to (3), in which the presentation unit simultaneously displays the plurality of images that displays the plurality of types of visualized information.

(5)

The information processing apparatus according to any of the above-described (1) to (4), in which the presentation unit displays the visualized information representing the plurality of types of analysis results associated with a selected item, during selection of the item among the plurality of items related to skin conditions.

(6)

The information processing apparatus according to the above-described (5), in which, in a case where a pore item is selected, the presentation unit displays the visualized information representing the analysis result of pore opening and the visualized information representing the analysis result of pore blackhead.

(7)

The information processing apparatus according to the above-described (5), in which, in a case where a spot item is selected, the presentation unit displays individually the visualized information representing the analysis result of different types of spots.

(8)

The information processing apparatus according to any of the above-described (1) to (7), further including an analysis unit configured to analyze skin conditions on the basis of the image of the skin.

(9)

The information processing apparatus according to the above-described (8), in which the analysis unit calculates the amount of a predetermined component of the skin at individual positions on the skin image, specifies a position on which the amount of predetermined component is locally large on the basis of the amount of predetermined component, and outputs information representing the amount of predetermined component in a region including the specified position, as the analysis result.

(10)

An information processing method including:

obtaining information representing a plurality of types of analysis results on skin conditions obtained by analyzing an image of a skin at a same position, and simultaneously displaying, on a same image, a plurality of types of visualized information obtained from visualized representation of the plurality of types of analysis results.

(11)

A program that causes a computer to execute processing including:

obtaining information representing a plurality of types of analysis results of skin conditions obtained by analyzing an image of a skin at a same position, and simultaneously displaying, on a same image, a plurality of types of visualized information obtained from visual representation of the plurality of types of analysis results.

REFERENCE SIGNS LIST

1 Information processing terminal
2 Skin measurement instrument
3 Analysis server
51 Display
231 Skin image acquisition unit
232 Communication control unit
233 Display control unit
271 Skin image acquisition unit
272 Skin analysis unit
273 Analysis result acquisition unit
274 Presentation unit
281 Pore analysis unit
282 Spot analysis unit

The invention claimed is:

1. An information processing apparatus comprising:
a processing device and a memory containing instructions that, when executed by the processing device, are configured to:
obtain information representing a plurality of types of analysis results of skin conditions obtained by analyzing an image of a skin at a same position, and
simultaneously display, on a same image, a plurality of types of visualized information obtained from visualized representation of the plurality of types of analysis results, wherein the plurality of types of visualized information include, on the same image, an analysis results display image that represents the analysis results and an illustration of a face that indicates a position on the face represented by the analysis results, wherein a plurality of icons are superimposed on the illustration of the face and wherein each icon of the plurality of icons includes a score indicating a skin condition at a position of the icon on the illustration of the face and is selectable to display an analysis result corresponding to the selected icon.

2. The information processing apparatus according to the claim 1,
wherein the visualized information is displayed on the image of the skin used for obtaining the analysis result.

3. The information processing apparatus according to claim 1,
wherein the visualized information representing the plurality of types of analysis results obtained by analyzing the image of the skin at a selected position, is displayed in accordance with the selection of the position of the skin.

4. The information processing apparatus according to claim 1,
wherein the plurality of images that display the plurality of types of visualized information are simultaneously displayed.

5. The information processing apparatus according to claim 1,
wherein the visualized information representing the plurality of types of analysis results associated with a selected item, is displayed during selection of the item among the plurality of items related to skin conditions.

6. The information processing apparatus according to claim 5,
wherein, in a case where a pore item is selected, the visualized information representing the analysis result of pore opening and the visualized information representing the analysis result of pore blackhead are displayed.

7. The information processing apparatus according to claim 5,
wherein, in a case where a spot item is selected, the visualized information representing the analysis result of different types of spots is displayed individually.

8. The information processing apparatus according to claim 1,
wherein the instructions are further configured to analyze skin conditions on the basis of the image of the skin.

9. The information processing apparatus according to claim 8,
wherein the analysis instructions are configured to calculate the amount of a predetermined component of the skin at individual positions on the skin image, specify a position on which the amount of predetermined component is locally large on the basis of the amount of predetermined component, and output information representing the amount of predetermined component in a region including the specified position, as the analysis result.

10. An information processing method performed by an information processing apparatus, the method comprising:
obtaining information representing a plurality of types of analysis results on skin conditions obtained by analyzing an image of a skin at a same position, and
simultaneously displaying, on a same image, a plurality of types of visualized information obtained from visualized representation of the plurality of types of analysis results, wherein the plurality of types of visualized information include, on the same image, an analysis results display image that represents the analysis results and an illustration of a face that indicates a position on the face represented by the analysis results, wherein a plurality of icons are superimposed on the illustration of the face and wherein each icon of the plurality of icons includes a score indicating a skin condition at a position of the icon on the illustration of the face and is selectable to display an analysis result corresponding to the selected icon.

11. A non-transitory computer-readable medium containing instructions that, when executed by a processing device, perform an information processing method comprising:
obtaining information representing a plurality of types of analysis results on skin conditions obtained by analyzing an image of a skin at a same position, and
simultaneously displaying, on a same image, a plurality of types of visualized information obtained from visualized representation of the plurality of types of analysis results, wherein the plurality of types of visualized information include, on the same image, an analysis results display image that represents the analysis results and an illustration of a face that indicates a position on the face represented by the analysis results, wherein a plurality of icons are superimposed on the illustration of the face and wherein each icon of the plurality of icons includes a score indicating a skin condition at a position of the icon on the illustration of the face and is selectable to display an analysis result corresponding to the selected icon.

* * * * *